United States Patent
Puschl et al.

(10) Patent No.: US 8,927,738 B2
(45) Date of Patent: *Jan. 6, 2015

(54) 2-ARYLIMIDAZOLE DERIVATIVES AS PDE10A ENZYME INHIBITORS

(71) Applicant: H. Lundbeck A/S, Valby-Copenhagen (DK)

(72) Inventors: Ask Puschl, Frederiksberg (DK); Jacob Nielsen, Kobenhavn V (DK); Jan Kehler, Lyngby (DK); John Paul Kilburn, Haslev (DK); Mauro Marigo, Skovlunde (DK); Morton Langgard, Glostrup (DK)

(73) Assignee: H. Lundbeck A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/924,712

(22) Filed: Jun. 24, 2013

(65) Prior Publication Data

US 2013/0289038 A1    Oct. 31, 2013

Related U.S. Application Data

(63) Continuation of application No. 13/515,325, filed as application No. PCT/DK2010/050343 on Dec. 15, 2010, now Pat. No. 8,501,797.

(60) Provisional application No. 61/287,324, filed on Dec. 17, 2009.

(30) Foreign Application Priority Data

Dec. 17, 2009   (DK) .................................. 2009 01341

(51) Int. Cl.
| C07D 233/64 | (2006.01) |
| C07D 487/04 | (2006.01) |
| C07D 471/04 | (2006.01) |

(52) U.S. Cl.
CPC ............ C07D 487/04 (2013.01); C07D 471/04 (2013.01)
USPC ........... 548/335.1; 544/350; 548/202; 549/59

(58) Field of Classification Search
CPC .................................................... C07D 233/64
USPC ................... 544/350; 548/202, 335.1; 549/59
See application file for complete search history.

(56) References Cited

U.S. PATENT DOCUMENTS

| 7,897,619 B2 | 3/2011 | Zeng et al. |
| 2012/0302548 A1 | 11/2012 | Puschl et al. |

FOREIGN PATENT DOCUMENTS

| WO | 2004/014881 A2 | 2/2004 |
| WO | 2007/129183 A2 | 11/2007 |
| WO | 2008/004117 A1 | 1/2008 |
| WO | 2009/152825 A1 | 12/2009 |
| WO | 2011/072694 A1 | 6/2011 |
| WO | 2011/072696 A1 | 6/2011 |
| WO | 2011/072697 A1 | 6/2011 |

OTHER PUBLICATIONS

Hackam et al., 2006, "Translation of Research Evidence From Animals to Humans" JAMA, 296(14), 1731-1732.
Jordan, V.C. 2003, "Tamoxifen: A Most Unlikely Pioneering Medicine", Nature Reviews: Drug Discovery, 2, 205-213.
Kehler et al., 2009, "Patented PDE10A inhibitors: Novel compounds since 2007", Expert Opinion on Therapeutics Patents, Informa Healthcare, vol. 19, No. 12, pp. 1715-1725.
Geyer MA and Moghaddam B., 2002, "Animal Models Relevant to Schizophrenia Disorders" Neurospsychopharmacology: The Fifth Generation of Progress, Edited by Kenneth L. Davis, Dennis Charney, Joseph T. Coyle, and Charles Nemeroff, American College of Neuropschopharmacology, pp. 689-701.
Jackson DM et al., 1994, "Dopamine receptor antagonists block amphetamine and phencyclidine-induced motor stimulation in rats," Pharrmacol Biochem Behav. 48(2):465-71.
Jentsch JD and Roth RH., 1999 The neuropsychopharmacology of phencyclidine: from NMDA receptor hypofunction to the dopamine hypothesis of schizophrenia, Neuropsychopharmacology, 20(3):201-225.
Japanese Office Action issued in connection with Japanese Application No. 2012-543476, issued on Oct. 14, 2014.

*Primary Examiner* — Douglas M Willis
(74) *Attorney, Agent, or Firm* — Mary Catherine Di Nunzio

(57) ABSTRACT

This invention is directed to compounds of formula I having the structure

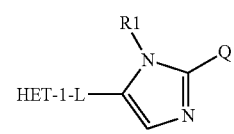

which are PDE10A enzyme inhibitors. The invention provides a pharmaceutical composition comprising a therapeutically effective amount of a compound of the invention and a pharmaceutically acceptable carrier. The present invention also provides processes for the preparation of the compounds of formula I. The present invention further provides a method of treating a subject suffering from a neurodegenerative disorder comprising administering to the subject a therapeutically effective amount of a compound of formula I. The present invention also provides a method of treating a subject suffering from a drug addiction comprising administering to the subject a therapeutically effective amount of a compound of formula I. The present invention further provides a method of treating a subject suffering from a psychiatric disorder comprising administering to the subject a therapeutically effective amount of a compound of formula I.

7 Claims, No Drawings

2-ARYLIMIDAZOLE DERIVATIVES AS PDE10A ENZYME INHIBITORS

CROSS-REFERENCE TO RELATED APPLICATIONS

This present application is a Continuation of National Stage application Ser. No. 13/515,325 filed Aug. 15, 2012, which is claims priority of International Application No. PCT/DK2010/050343, filed Dec. 15, 2010, which claims priority of U.S. Provisional Application No. 61/287,324, filed Dec. 17, 2009 and Danish Application No. PA200901341, filed Dec. 17, 2009. Each of these applications is hereby incorporated by reference in its entirety.

FIELD OF THE INVENTION

The present invention provides heteroaromatic compounds that are PDE10A enzyme inhibitors, and as such are useful to treat neurodegenerative and psychiatric disorders. Especially, the invention provides compounds that are highly selective for PDE10 over other PDE subtypes. The present invention also provides pharmaceutical compositions comprising compounds of the invention and methods of treating disorders using the compounds of the invention.

BACKGROUND OF THE INVENTION

Throughout this application, various publications are referenced in full. The disclosures of these publications are hereby incorporated by reference into this application to describe more fully the state of the art to which this invention pertains.

The cyclic nucleotides cyclic-adenosine monophosphate (cAMP) and cyclic-guanosine monophosphate (cGMP) function as intracellular second messengers regulating a vast array of processes in neurons. Intracellular cAMP and cGMP are generated by adenyl and guanyl cyclases, and are degraded by cyclic nucleotide phosphodiesterases (PDEs). Intracellular levels of cAMP and cGMP are controlled by intracellular signaling, and stimulation/repression of adenyl and guanyl cyclases in response to GPCR activation is a well characterized way of controlling cyclic nucleotide concentrations (Antoni, F. A. *Front. Neuroendocrinol.* 2000, 21, 103-132). cAMP and cGMP levels in turn control activity of cAMP- and cGMP-dependent kinases as well as other proteins with cyclic nucleotide response elements, which through subsequent phosphorylation of proteins and other processes regulate key neuronal functions such as synaptic transmission, neuronal differentiation and survival.

There are 21 phosphodiesterase genes that can be divided into 11 gene families. There are ten families of adenylyl cyclases, two of guanylyl cyclases, and eleven of phosphodiesterases. PDEs are a class of intracellular enzymes that regulate levels of cAMP and cGMP via hydrolysis of the cyclic nucleotides into their respective nucleotide monophosphates. Some PDEs degrade cAMP, some cGMP and some both. Most PDEs have a widespread expression and have roles in many tissues, while some are more tissue-specific.

Phosphodiesterase 10A (PDE10A) is a dual-specificity phosphodiesterase that can convert both cAMP to AMP and cGMP to GMP (Loughney, K. et al. *Gene* 1999, 234, 109-117; Fujishige, K. et al. *Eur. J. Biochem.* 1999, 266, 1118-1127 and Soderling, S. et al. *Proc. Natl. Acad. Sci.* 1999, 96, 7071-7076). PDE10A is primarily expressed in the neurons in the striatum, n. accumbens and in the olfactory tubercle (Kotera, J. et al. *Biochem. Biophys. Res. Comm.* 1999, 261, 551-557 and Seeger, T. F. et al. *Brain Research,* 2003, 985, 113-126).

Mouse PDE10A is the first identified member of the PDE10 family of phosphodiesterases (Fujishige, K. et al. *J. Biol. Chem.* 1999, 274, 18438-18445 and Loughney, K. et al. *Gene* 1999, 234, 109-117) and N-terminal splice variants of both the rat and human genes have been identified (Kotera, J. et al. *Biochem. Biophys. Res. Comm.* 1999, 261, 551-557 and Fujishige, K. et al. *Eur. J. Biochem.* 1999, 266, 1118-1127). There is a high degree of homology across species. PDE10A is uniquely localized in mammals relative to other PDE families. mRNA for PDE10 is highly expressed in testis and brain (Fujishige, K. et al. *Eur J Biochem.* 1999, 266, 1118-1127; Soderling, S. et al. *Proc. Natl. Acad. Sci.* 1999, 96, 7071-7076 and Loughney, K. et al. *Gene* 1999, 234, 109-117). These studies indicate that within the brain, PDE10 expression is highest in the striatum (caudate and putamen), n. accumbens and olfactory tubercle. More recently, an analysis has been made of the expression pattern in rodent brain of PDE10A mRNA (Seeger, T. F. et al. *Abst. Soc. Neurosci.* 2000, 26, 345.10) and PDE10A protein (Menniti, F. S. et al. William Harvey Research Conference 'Phosphodiesterase in Health and Disease', Porto, Portugal, Dec. 5-7, 2001).

PDE10A is expressed at high levels by the medium spiny neurons (MSN) of the caudate nucleus, the accumbens nucleus and the corresponding neurons of the olfactory tubercle. These constitute the core of the basal ganglia system. The MSN has a key role in the cortical-basal ganglia-thalamocortical loop, integrating convergent cortical/thalamic input, and sending this integrated information back to the cortex. MSN express two functional classes of neurons: the $D_1$ class expressing $D_1$ dopamine receptors and the $D_2$ class expressing $D_2$ dopamine receptors. The $D_1$ class of neurons is part of the 'direct' striatal output pathway, which broadly functions to facilitate behavioral responses. The $D_2$ class of neurons is part of the 'indirect' striatal output pathway, which functions to suppress behavioral responses that compete with those being facilitated by the 'direct' pathway. These competing pathways act like the brake and accelerator in a car. In the simplest view, the poverty of movement in Parkinson's disease results from over-activity of the 'indirect' pathway, whereas excess movement in disorders such as Huntington's disease represent over-activity of the direct pathway. PDE10A regulation of cAMP and/or cGMP signaling in the dendritic compartment of these neurons may be involved in filtering the cortico/thalamic input into the MSN. Furthermore, PDE10A may be involved in the regulation of GABA release in the substantia nigra and globus pallidus (Seeger, T. F. et al. *Brain Research,* 2003, 985, 113-126).

Dopamine $D_2$ receptor antagonism is well established in the treatment of schizophrenia. Since the 1950's, dopamine $D_2$ receptor antagonism has been the mainstay in psychosis treatment and all effective antipsychotic drugs antagonise $D_2$ receptors. The effects of $D_2$ are likely to be mediated primarily through neurons in the striatum, n. accumbens and olfactory tubercle, since these areas receive the densest dopaminergic projections and have the strongest expression of $D_2$ receptors (Konradi, C. and Heckers, S. *Society of Biological Psychiatry,* 2001, 50, 729-742). Dopamine $D_2$ receptor agonism leads to decrease in cAMP levels in the cells where it is expressed through adenylate cyclase inhibition, and this is a component of $D_2$ signalling (Stoof, J. C.; Kebabian J. W. *Nature* 1981, 294, 366-368 and Neve, K. A. et al. *Journal of Receptors and Signal Transduction* 2004, 24, 165-205). Conversely, $D_2$ receptor antagonism effectively increases cAMP levels, and this effect could be mimicked by inhibition of cAMP degrading phosphodiesterases.

Most of the 21 phosphodiesterase genes are widely expressed; therefore inhibition is likely to have side effects. Because PDE10A, in this context, has the desired expression profile with high and relatively specific expression in neurons in striatum, n. accumbens and olfactory tubercle, PDE10A inhibition is likely to have effects similar to $D_2$ receptor antagonism and therefore have antipsychotic effects.

While PDE10A inhibition is expected to mimic $D_2$ receptor antagonism in part, it might be expected to have a different profile. The $D_2$ receptor has signalling components besides cAMP (Neve, K. A. et al. *Journal of Receptors and Signal Transduction* 2004, 24, 165-205), wherefore interference with cAMP through PDE10A inhibition may negatively modulate rather than directly antagonise dopamine signaling through $D_2$ receptors. This may reduce the risk of the extrapyrimidal side effects that are seen with strong $D_2$ antagonism. Conversely, PDE10A inhibition may have some effects not seen with $D_2$ receptor antagonism. PDE10A is also expressed in $D_1$ receptors expressing striatal neurons (Seeger, T. F. et al. *Brain Research*, 2003, 985, 113-126). Since $D_1$ receptor agonism leads to stimulation of adenylate cyclase and resulting increase in cAMP levels, PDE10A inhibition is likely to also have effects that mimic $D_1$ receptor agonism. Finally, PDE10A inhibition will not only increase cAMP in cells, but might also be expected to increase cGMP levels, since PDE10A is a dual specificity phosphodiesterase. cGMP activates a number of target protein in cells like cAMP and also interacts with the cAMP signalling pathways. In conclusion, PDE10A inhibition is likely to mimic $D_2$ receptor antagonism in part and therefore has antipsychotic effect, but the profile might differ from that observed with classical $D_2$ receptor antagonists.

The PDE10A inhibitor papaverine is shown to be active in several antipsychotic models. Papaverine potentiated the cataleptic effect of the $D_2$ receptor antagonist haloperidol in rats, but did not cause catalepsy on its own (WO 03/093499). Papaverine reduced hyperactivity in rats induced by PCP, while reduction of amphetamine induced hyperactivity was insignificant (WO 03/093499). These models suggest that PDE10A inhibition has the classic antipsychotic potential that would be expected from theoretical considerations. WO 03/093499 further discloses the use of selective PDE10 inhibitors for the treatment of associated neurologic and psychiatric disorders. Furthermore, PDE10A inhibition reverses subchronic PCP-induced deficits in attentional set-shifting in rats (Rodefer et al. *Eur. J. Neurosci.* 2005, 4, 1070-1076). This model suggests that PDE10A inhibition might alleviate cognitive deficits associated with schizophrenia.

The tissue distribution of PDE10A indicates that PDE10A inhibitors can be used to raise levels of cAMP and/or cGMP within cells that express the PDE10 enzyme, especially neurons that comprise the basal ganglia, and the PDE10A inhibitors of the present invention would therefore be useful in treating a variety of associated neuropsychiatric conditions involving the basal ganglia such as neurological and psychiatric disorders, schizophrenia, bipolar disorder, obsessive compulsive disorder, and the like, and may have the benefit of not possessing unwanted side effects, which are associated with the current therapies on the market.

Furthermore, recent publications (WO 2005/120514, WO 2005012485, Cantin et al, Bioorganic & Medicinal Chemistry Letters 17 (2007) 2869-2873) suggest that PDE10A inhibitors may be useful for treatment of obesity and non-insulin dependent diabetes.

With respect to inhibitors of PDE10A, EP 1250923 discloses the use of selective PDE10 inhibitors in general, and papaverine in particular, for the treatment of certain neurologic and psychiatric disorders.

WO 05/113517 discloses benzodiazepine stereospecific compounds as inhibitors of phosphodiesterase, especially types 2 and 4, and the prevention and treatment of pathologies involving a central and/or peripheral disorder. WO 02/88096 discloses benzodiazepine derivatives and their uses as inhibitors of phosphodiesterase, especially type 4 in the therapeutic field. WO 04/41258 discloses benzodiazepinone derivatives and their uses as inhibitors of phosphodiesterase, especially type 2 in the therapeutic field.

Pyrrolodihydroisoquinolines and variants thereof are disclosed as inhibitors of PDE10 in WO 05/03129 and WO 05/02579. Piperidinyl-substituted quinazolines and isoquinolines that serve as PDE10 inhibitors are disclosed in WO 05/82883. WO 06/11040 discloses substituted quinazoline and isoquinoline compounds that serve as inhibitors of PDE10. US 20050182079 discloses substituted tetrahydroisoquinolinyl derivatives of quinazoline and isoquinoline that serve as effective phosphodiesterase (PDE) inhibitors. In particular, US 20050182079 relates to said compounds, which are selective inhibitors of PDE10. Analogously, US 20060019975 discloses piperidine derivatives of quinazoline and isoquinoline that serve as effective phosphodiesterase (PDE) inhibitors. US 20060019975 also relates to compounds that are selective inhibitors of PDE10. WO 06/028957 discloses cinnoline derivatives as inhibitors of phosphodiesterase type 10 for the treatment of psychiatric and neurological syndromes.

However, these disclosures do not pertain to the compounds of the invention, which are structurally unrelated to any of the known PDE10 inhibitors (Kehler, J. et al. *Expert Opin. Ther. Patents* 2007, 17, 147-158 and Kehler, J. et al. *Expert Opin. Ther. Patents* 2009, 19, 1715-1725), and which have now been found by the inventors to be highly active and selective PDE10A enzyme inhibitors.

The compounds of the invention may offer alternatives to current marketed treatments for neurodegenerative and/or psychiatric disorders, which are not efficacious in all patients. Hence, there remains a need for alternative methods of treatment.

SUMMARY OF THE INVENTION

The objective of the present invention is to provide compounds that are selective PDE10A enzyme inhibitors.

A further objective of the present invention is to provide compounds which have such activity, and which have improved solubility, metabolic stability and/or bioavailability compared to prior art compounds.

Another objective of the invention is to provide an effective treatment, in particular long-term treatment, of a human patient, without causing the side effects typically associated with current therapies for neurological and psychiatric disorders.

Further objectives of the invention will become apparent upon reading the present specification.

Accordingly, in one aspect the present invention relates to compounds of formula I:

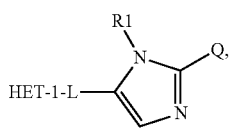

wherein HET-1 is a heteroaromatic group of formula II containing from 2 to 4 nitrogen atoms:

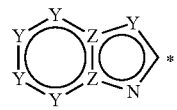

wherein Y can be N or CH, Z can be N or C, and wherein HET-1 may optionally be substituted with up to three substituents R7, R8 and R9 individually selected from H; $C_1$-$C_6$ alkyl such as Me; halogen such as chlorine and bromine; cyano; halo($C_1$-$C_6$)alkyl such as trifluoromethyl; aryl such as phenyl; alkoxy, such as methoxy, dimethoxy, ethoxy, methoxy-ethoxy and ethoxy-methoxy, and $C_1$-$C_6$ hydroxyalkyl such as $CH_2CH_2OH$, and wherein * denotes the attachment point, -L- is a linker selected from $—S—CH_2—$, $—CH_2—S—$, $—CH_2—CH_2—$, $—CH=CH—$, and $—C\equiv C—$;

R1 is selected from H; $C_1$-$C_6$ alkyl such as methyl, ethyl, 1-propyl, 2-propyl, isobutyl; $C_1$-$C_6$ alkyl($C_3$-$C_8$)cycloalkyl such as cyclopropylmethyl; $C_1$-$C_6$ hydroxyalkyl such as hydroxyethyl; $CH_2CN$; $CH_2C(O)NH_2$; $C_1$-$C_6$ arylalkyl such as benzyl and 4-chlorobenzyl; and $C_1$-$C_6$ alkyl-heterocycloalkyl such as tetrahydropyran-4-yl-methyl and 2-morpholin-4-yl-ethyl;

wherein Q is a phenyl, optionally substituted with 1, 2 or three substituents or Q is a monocyclic 5-membered or 6-membered heteroaromatic group containing 1 or 2 heteroatoms, preferred Q is chosen among structures of the formula, wherein "*" denotes the attachment point:

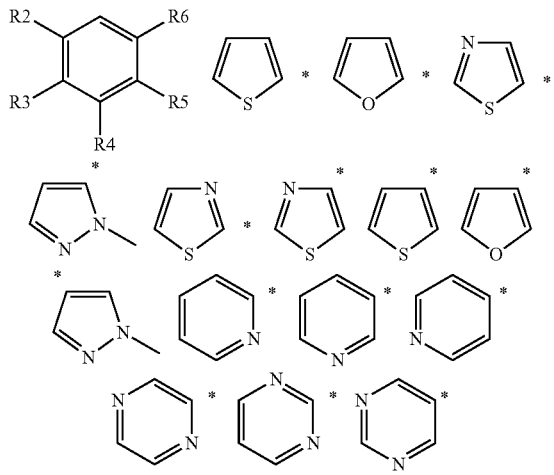

Wherein R2-R6 is each selected independently from H; $C_1$-$C_6$ alkoxy such as methoxy; and halogen such as chlorine or fluorine;

and tautomers and pharmaceutically acceptable salts thereof, and polymorphic forms thereof.

In separate embodiments of the invention, the compound of formula I is selected among the specific compounds disclosed in the Experimental Section herein.

The invention further provides a compound of formula I, or a pharmaceutically acceptable salt thereof, for use as a medicament.

In another aspect, the present invention provides a pharmaceutical composition comprising a therapeutically effective amount of a compound of formula I and a pharmaceutically acceptable carrier, diluent or excipient.

The invention further provides the use of a compound of formula I, or a pharmaceutically acceptable salt thereof, for the preparation of a medicament for the treatment of a neurodegenerative or psychiatric disorder.

Furthermore, in yet another aspect, the present invention provides a method of treating a subject suffering from a neurodegenerative disorder, comprising administering to the subject a therapeutically effective amount of a compound of formula I. In a still further aspect, the present invention provides a method of treating a subject suffering from a psychiatric disorder, comprising administering to the subject a therapeutically effective amount of a compound of formula I. In another embodiment, the present invention provides a method of treating a subject suffering from a drug addiction, such as an alcohol, amphetamine, cocaine, or opiate addiction.

DETAILED DESCRIPTION OF THE INVENTION

Definition of Substitutents

As used in the context of the present invention, the terms "halo" and "halogen" are used interchangeably and refer to fluorine, chlorine, bromine or iodine.

The term "$C_1$-$C_6$ alkyl" refers to a straight-chain or branched saturated hydrocarbon having from one to six carbon atoms, inclusive. Examples of such groups include, but are not limited to, methyl, ethyl, 1-propyl, 2-propyl, 1-butyl, 2-butyl, 2-methyl-2-propyl, 2-methyl-1-butyl, and n-hexyl. The expression "$C_1$-$C_6$ hydroxyalkyl" refers to a $C_1$-$C_6$ alkyl group as defined above which is substituted with one hydroxy group. The term "halo($C_1$-$C_6$)alkyl" refers to a $C_1$-$C_6$ alkyl group as defined above which is substituted with up to three halogen atoms, such as trifluoromethyl.

The expression "$C_1$-$C_6$ alkoxy" refers to a straight-chain or branched saturated alkoxy group having from one to six carbon atoms, inclusive, with the open valency on the oxygen. Examples of such groups include, but are not limited to, methoxy, ethoxy, n-butoxy, 2-methyl-pentoxy and n-hexyloxy.

The term "$C_3$-$C_8$ cycloalkyl" typically refers to cyclopropyl, cyclobutyl, cyclopentyl, cyclohexyl, cycloheptyl or cyclooctyl. The expression "$C_1$-$C_6$ alkyl($C_3$-$C_8$)cycloalkyl" refers to a $C_3$-$C_8$ cycloalkyl as defined above which is substituted with a straight-chain or branched $C_1$-$C_6$ alkyl. Examples of such groups include, but are not limited to, cyclopropylmethyl.

The term "heterocycloalkyl" refers to a four to eight membered ring containing carbon atoms and up to three N, O or S atoms, provided that the four to eight membered ring does not contain adjacent O or adjacent S atoms. The open valency is on either the heteroatom or carbon atom. Examples of such groups include, but are not limited to, azetidinyl, oxetanyl, piperazinyl, morpholinyl, thiomorpholinyl and [1,4]diazepanyl. The term "hydroxyheterocycloalkyl" refers to a heterocycloalkyl as defined above which is substituted with one hydroxy group. The term "$C_1$-$C_6$ alkyl-heterocycloalkyl" refers to a heterocycloalkyl as defined above which is substituted with a $C_1$-$C_6$ alkyl group. Examples of such groups include, but are not limited to, tetrahydropyran-4-yl-methyl and 2-morpholin-4-yl-ethyl.

The term "aryl" refers to a phenyl ring, optionally substituted with halogen, $C_1$-$C_6$ alkyl, $C_1$-$C_6$ alkoxy or halo($C_1$-$C_6$) alkyl as defined above. Examples of such groups include, but are not limited to, phenyl and 4-chlorophenyl.

The term "$C_1$-$C_6$arylalkyl" refers to an aryl as defined above which is substituted with a straight-chain or branched $C_1$-$C_6$ alkyl. Examples of such groups include, but are not limited to, benzyl and 4-chlorobenzyl.

Additionally, the present invention further provides certain embodiments of the invention, that are described below.

In one embodiment of the invention, HET-1 is a heteroaromatic group of formula II containing 2 nitrogen atoms. In another embodiment of the invention, HET-1 is a heteroaromatic group of formula II containing 3 nitrogen atoms. In yet another embodiment of the invention, HET-1 is a heteroaromatic group of formula II containing 4 nitrogen atoms.

HET-1 is preferably chosen among the following heteroaromatic groups, wherein "*" denotes the attachment point:

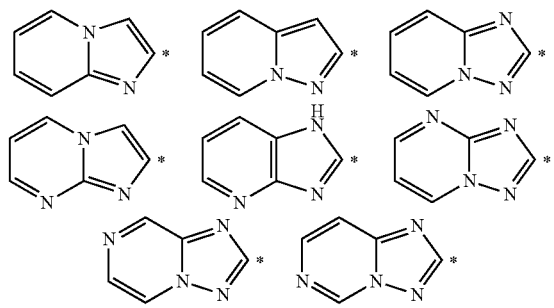

In a further embodiment one or more of the hydrogen atoms of the compound of formula I have been substituted by deuterium. In particular hydrogen has been replaced by deuterium when $R_7$-$R_9$ is methyl or methoxy.

In separate embodiments of the invention, the compound of formula I is selected among the following specific compounds, in the form of the free base, one or more tautomers thereof or a pharmaceutically acceptable salt thereof. Table 1 lists compounds of the invention and the corresponding $IC_{50}$ values determined as described in the section "PDE10A inhibition assay". Each of the compounds constitutes an individual embodiment, of the present invention.

It should be understood that the various aspects, embodiments, implementations and features of the invention mentioned herein may be claimed separately, or in any combination, as illustrated by the following non-limiting examples.

TABLE 1

Compounds of the invention and $IC_{50}$ values

| Compound | IC50 (nM) |
|---|---|
| 8-Methoxy-5-methyl-2-[2-(2-phenyl-1H-imidazol-4-yl)-ethyl]-[1,2,4]triazolo[1,5-a]pyridine | 5.9 |
| 8-Methoxy-5-methyl-2-[2-(1-methyl-2-phenyl-1H-imidazol-4-yl)-ethyl]-[1,2,4]triazolo[1,5-a]pyridine | 79 |
| 8-Ethyl-5-methyl-2-[2-(1-methyl-2-phenyl-1H-imidazol-4-yl)-ethyl]-[1,2,4]triazolo[1,5-a]pyridine | 23 |
| 5,8-Dimethyl-2-[2-(2-phenyl-1H-imidazol-4-yl)-ethyl]-[1,2,4]triazolo[1,5-a]pyrazine | 4.2 |

TABLE 1-continued

Compounds of the invention and $IC_{50}$ values

| Compound | IC50 (nM) |
|---|---|
| 5,8-Dimethyl-2-[2-(1-methyl-2-phenyl-1H-imidazol-4-yl)-ethyl]-[1,2,4]triazolo[1,5-a]pyrazine | 45 |
| 8-Methoxy-5-methyl-2-[2-(1-methyl-2-thiophen-2-yl-1H-imidazol-4-yl)-ethyl]-[1,2,4]triazolo[1,5-a]pyridine | 9.0 |
| 5,8-Dimethyl-2-[2-(1-methyl-2-thiophen-2-yl-1H-imidazol-4-yl)-ethyl]-[1,2,4]triazolo[1,5-a]pyrazine | 1.0 |
| 5,8-Dimethyl-2-[2-(1-methyl-2-thiazol-2-yl-1H-imidazol-4-yl)-ethyl]-[1,2,4]triazolo[1,5-a]pyrazine | 7.7 |
| 5,8-Dimethyl-2-[2-(2-thiazol-5-yl-1H-imidazol-4-yl)-ethyl]-[1,2,4]triazolo[1,5-a]pyrazine | 6.5 |
| 5,8-Dimethyl-2-[2-(2-thiazol-5-yl-1H-imidazol-4-yl)-ethyl]-[1,2,4]triazolo[1,5-a]pyridine | 3.1 |
| 5,8-Dimethyl-2-[2-(1-methyl-2-thiazol-5-yl-1H-imidazol-4-yl)-ethyl]-[1,2,4]triazolo[1,5-a]pyrazine | 22 |
| 2-[2-(2-Furan-2-yl-1-methyl-1H-imidazol-4-yl)-ethyl]-5,8-dimethyl-[1,2,4]triazolo[1,5-a]pyrazine | 1.1 |
| 5,8-Dimethyl-2-[2-(2-thiazol-4-yl-1H-imidazol-4-yl)-ethyl]-[1,2,4]triazolo[1,5-a]pyrazine | 3.5 |
| 5,8-Dimethyl-2-[2-(2-thiazol-4-yl-1H-imidazol-4-yl)-ethyl]-[1,2,4]triazolo[1,5-a]pyridine | 3.5 |
| 2-[2-(2-Furan-2-yl-1-methyl-1H-imidazol-4-yl)-ethyl]-5,8-dimethyl-[1,2,4]triazolo[1,5-a]pyridine | 0.75 |
| 5,8-Dimethyl-2-[2-(2-thiophen-2-yl-1H-imidazol-4-yl)-ethyl]-[1,2,4]triazolo[1,5-a]pyridine | 0.34 |
| 5,8-Dimethyl-2-[2-(2-thiazol-2-yl-1H-imidazol-4-yl)-ethyl]-[1,2,4]triazolo[1,5-a]pyridine | 1.6 |
| 2-[2-(2-Furan-2-yl-1H-imidazol-4-yl)-ethyl]-5,8-dimethyl-[1,2,4]triazolo[1,5-a]pyridine | 0.62 |
| 2-[2-(2-Furan-3-yl-1H-imidazol-4-yl)-ethyl]-5,8-dimethyl-[1,2,4]triazolo[1,5-a]pyridine | 0.65 |
| 5,8-Dimethyl-2-[2-(2-thiophen-2-yl-1H-imidazol-4-yl)-ethyl]-[1,2,4]triazolo[1,5-a]pyrazine | 0.4 |
| 5,8-Dimethyl-2-[2-(2-thiazol-2-yl-1H-imidazol-4-yl)-ethyl]-[1,2,4]triazolo[1,5-a]pyrazine | 0.63 |
| 2-[2-(2-Furan-3-yl-1H-imidazol-4-yl)-ethyl]-5,8-dimethyl-[1,2,4]triazolo[1,5-a]pyrazine | 0.27 |
| 2-[2-(2-Furan-2-yl-1H-imidazol-4-yl)-ethyl]-5,8-dimethyl-[1,2,4]triazolo[1,5-a]pyrazine | 0.97 |
| 5,8-Dimethyl-2-{2-[1-methyl-2-(5-methyl-furan-2-yl)-1H-imidazol-4-yl]-ethyl}-[1,2,4]triazolo[1,5-a]pyrazine | 3.5 |
| 5,8-Dimethyl-2-[2-(1-methyl-2-thiazol-4-yl-1H-imidazol-4-yl)-ethyl]-[1,2,4]triazolo[1,5-a]pyrazine | 11 |
| 2-{2-[2-(4-Fluoro-phenyl)-1H-imidazol-4-yl]-ethyl}-5,8-dimethyl-[1,2,4]triazolo[1,5-a]pyrazine | 12 |

In a particular embodiment of the present invention the compounds of the present invention have an $IC_{50}$ value of less than 50 nM, such as in the range of 0.2-20 nM, particularly in the range of 0.2-10 nM, such as in the range of 0.2-5 nM or in the range of 0.2-1 nM.

Pharmaceutically Acceptable Salts

The present invention also comprises salts of the compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., *J. Pharm. Sci.* 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Pharmaceutical Compositions

The present invention further provides a pharmaceutical composition comprising a therapeutically effective amount of a compound of formula I and a pharmaceutically acceptable carrier or diluent. The present invention also provides a pharmaceutical composition comprising a therapeutically effective amount of one of the specific compounds disclosed in the Experimental Section herein and a pharmaceutically acceptable carrier or diluent.

The compounds of the invention may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as oral, rectal, nasal, pulmonary, topical (including buccal and sublingual), transdermal, intracisternal, intraperitoneal, vaginal and parenteral (including subcutaneous, intramuscular, intrathecal, intravenous and intradermal) routes. It will be appreciated that the route will depend on the general condition and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs. Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day. Typical oral dosages further range from about 0.05 to about 10 mg/kg body weight per day. Oral dosages are usually administered in one or more dosages, typically, one to three dosages per day. The exact dosage will depend upon the frequency and mode of administration, the sex, age, weight and general condition of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

For parenteral routes such as intravenous, intrathecal, intramuscular and similar administration, typical doses are in the order of half the dose employed for oral administration.

The present invention also provides a process for making a pharmaceutical composition comprising admixing a therapeutically effective amount of a compound of formula I and at least one pharmaceutically acceptable carrier or diluent. In an embodiment, of the present invention, the compound utilized in the aforementioned process is one of the specific compounds disclosed in the Experimental Section herein.

The compounds of this invention are generally utilized as the free substance or as a pharmaceutically acceptable salt thereof. One example is an acid addition salt of a compound having the utility of a free base. When a compound of formula I contains a free base such salts are prepared in a conventional manner by treating a solution or suspension of a free base of formula I with a molar equivalent of a pharmaceutically acceptable acid. Representative examples of suitable organic and inorganic acids are described above.

For parenteral administration, solutions of the compounds of formula I in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compounds of formula I may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of formula I and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tableted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

The pharmaceutical compositions of the invention may be prepared by conventional methods in the art. For example, tablets may be prepared by mixing the active ingredient with ordinary adjuvants and/or diluents and subsequently compressing the mixture in a conventional tabletting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

Therapeutically Effective Amount

In the present context, the term "therapeutically effective amount" of a compound means an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the present context, the term "treatment" and "treating" means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatments are two separate aspects of the invention. The patient to be treated is preferably a mammal, in particular a human being.

Treatment of Disorders

As mentioned above, the compounds of formula I are PDE10A enzyme inhibitors and as such are useful to treat associated neurological and psychiatric disorders.

The invention thus provides a compound of formula I or a pharmaceutically acceptable acid addition salt thereof, as well as a pharmaceutical composition containing such a compound, for use in the treatment of a neurodegenerative disorder, psychiatric disorder or drug addiction in mammals including humans; wherein the neurodegenerative disorder is selected from the group consisting of Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline; and wherein the psychiatric disorder is selected from the group consisting of schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, *cannabis*, cocaine, hallucinogens, inhalants, opioids, or phencyclidine; personality disorder of the paranoid type; and personality disorder of the schizoid type; and wherein the drug addiction is an alcohol, amphetamine, cocaine, or opiate addiction.

The compounds of formula I or pharmaceutically acceptable salts thereof may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefore, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

The present invention provides a method of treating a mammal, including a human, suffering from a neurodegenerative disorder selected from a cognition disorder or movement disorder, which method comprises administering to the subject a therapeutically effective amount of a compound of formula I.

This invention further provides a method of treating a neurodegenerative disorder or condition in a mammal, including a human, which method comprises administering to said mammal an amount of a compound of formula I effective in inhibiting PDE10.

This invention also provides a method of treating a subject suffering from a psychiatric disorder, which method comprises administering to the subject a therapeutically effective amount of a compound of formula I. Examples of psychiatric disorders that can be treated according to the present invention include, but are not limited to, schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, *cannabis*, cocaine, hallucinogens, inhalants, opioids, or phencyclidine; personality disorder of the paranoid type; and personality disorder of the schizoid type; and the anxiety disorder is selected from panic disorder; agoraphobia; a specific phobia; social phobia; obsessive-compulsive disorder; post-traumatic stress disorder; acute stress disorder; and generalized anxiety disorder.

It has been found that the compounds of formula I or pharmaceutically acceptable salts thereof may advantageously be administered in combination with at least one neuroleptic agent (which may be a typical or an atypical antipsychotic agent) to provide improved treatment of psychiatric disorders such as schizophrenia. The combinations, uses and methods of treatment of the invention may also provide advantages in treatment of patients who fail to respond adequately or who are resistant to other known treatments.

The present invention thus provides a method of treating a mammal suffering from a psychiatric disorder, such as schizophrenia, which method comprises administering to the mammal a therapeutically effective amount of a compound of formula I, either alone or as combination therapy together with at least one neuroleptic agent.

The term "neuroleptic agent" as used herein refers to drugs, which have the effect on cognition and behaviour of antipsychotic agent drugs that reduce confusion, delusions, hallucinations, and psychomotor agitation in patients with psychoses. Also known as major tranquilizers and antipsychotic drugs, neuroleptic agents include, but are not limited to: typical antipsychotic drugs, including phenothiazines, further divided into the aliphatics, piperidines, and piperazines, thioxanthenes (e.g., cisordinol), butyrophenones (e.g., haloperidol), dibenzoxazepines (e.g., loxapine), dihydroindolones (e.g., molindone), diphenylbutylpiperidines (e.g., pimozide), and atypical antipsychotic drugs, including benzisoxazoles (e.g., risperidone), sertindole, olanzapine, quetiapine, osanetant and ziprasidone.

Particularly preferred neuroleptic agents for use in the invention are sertindole, olanzapine, risperidone, quetiapine, aripiprazole, haloperidol, clozapine, ziprasidone and osanetant.

The present invention further provides a method of treating a subject suffering from a cognition disorder, which method comprises administering to the subject a therapeutically effective amount of a compound of formula I. Examples of cognition disorders that can be treated according to the present invention include, but are not limited to, Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder; for example reading disorder, mathematics disorder, or a disorder of written expression; attention-deficit/hyperactivity disorder; and age-related cognitive decline.

This invention also provides a method of treating a movement disorder, which method comprises administering to the subject a therapeutically effective amount of a compound of formula I. Examples of movement disorders that can be treated according to the present invention include, but are not limited to, Huntington's disease and dyskinesia associated with dopamine agonist therapy. This invention further provides a method of treating a movement disorder selected from Parkinson's disease and restless leg syndrome, which comprises administering to the subject a therapeutically effective amount of a compound of formula I.

This invention also provides a method of treating a mood disorder, which method comprises administering to the subject a therapeutically effective amount of a compound of formula I. Examples of mood disorders and mood episodes that can be treated according to the present invention include, but are not limited to major depressive episode of the mild, moderate or severe type, a manic or mixed mood episode, a hypomanic mood episode; a depressive episode with atypical features; a depressive episode with melancholic features; a depressive episode with catatonic features; a mood episode with postpartum onset; post-stroke depression; major depressive disorder; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, for example bipolar I disorder, bipolar II disorder, and cyclothymic disorder. It is understood that a mood disorder is a psychiatric disorder.

This invention further provides a method of treating a drug addiction, for example an alcohol, amphetamine, cocaine, or opiate addiction, in a mammal, including a human, which method comprises administering to said mammal an amount of a compound of formula I effective in treating drug addiction.

This invention also provides a method of treating a drug addiction, for example an alcohol, amphetamine, cocaine, or opiate addiction, in a mammal, including a human, which method comprises administering to said mammal an amount of a compound of formula I effective in inhibiting PDE10.

The term "drug addiction", as used herein, means an abnormal desire for a drug and is generally characterized by motivational disturbances such a compulsion to take the desired drug and episodes of intense drug craving.

Drug addiction is widely considered a pathological state. The disorder of addiction involves the progression of acute drug use to the development of drug-seeking behavior, the vulnerability to relapse, and the decreased, slowed ability to respond to naturally rewarding stimuli. For example, The Diagnostic and Statistical Manual of Mental Disorders, Fourth Edition (DSM-IV) has categorized three stages of addiction: preoccupation/anticipation, binge/intoxication, and withdrawal/negative affect. These stages are characterized, respectively, everywhere by constant cravings and preoccupation with obtaining the substance; using more of the substance than necessary to experience the intoxicating effects; and experiencing tolerance, withdrawal symptoms, and decreased motivation for normal life activities.

This invention further provides a method of treating a disorder comprising as a symptom a deficiency in attention and/or cognition in a mammal, including a human, which method comprises administering to said mammal an amount of a compound of formula I effective in treating said disorder.

Other disorders that can be treated according to the present invention are obsessive/compulsive disorders, Tourette's syndrome and other tic disorders.

As used herein, and unless otherwise indicated, a "neurodegenerative disorder or condition" refers to a disorder or condition that is caused by the dysfunction and/or death of neurons in the central nervous system. The treatment of these disorders and conditions can be facilitated by administration of an agent which prevents the dysfunction or death of neurons at risk in these disorders or conditions and/or enhances the function of damaged or healthy neurons in such a way as to compensate for the loss of function caused by the dysfunction or death of at-risk neurons. The term "neurotrophic agent" as used herein refers to a substance or agent that has some or all of these properties.

Examples of neurodegenerative disorders and conditions that can be treated according to the present invention include, but are not limited to, Parkinson's disease; Huntington's disease; dementia, for example Alzheimer's disease, multi-infarct dementia, AIDS-related dementia, and Fronto temporal Dementia; neurodegeneration associated with cerebral trauma; neurodegeneration associated with stroke, neurodegeneration associated with cerebral infarct; hypoglycemia-induced neurodegeneration; neurodegeneration associated with epileptic seizure; neurodegeneration associated with neurotoxin poisoning; and multi-system atrophy.

In one embodiment of the present invention, the neurodegenerative disorder or condition involves neurodegeneration of striatal medium spiny neurons in a mammal, including a human.

In a further embodiment of the present invention, the neurodegenerative disorder or condition is Huntington's disease.

In another embodiment, the invention provides a method of treating a subject to reduce body fat or body weight, or to treat non-insuline demanding diabetes mellitus (NIDDM), metabolic syndrome, or glucose intolerance, comprising administering to a subject in need thereof a therapeutically effective amount of a compound of formula I. In preferred embodiments, the subject is human, the subject is overweight or obese and the antagonist is administered orally. In another preferred embodiment, the method further comprising administering a second therapeutic agent to the subject, preferably an anti-obesity agent, e.g., rimonabant, orlistat, sibutramine, bromocriptine, ephedrine, leptin, pseudoephedrine, or peptide YY3-36, or analogs thereof.

The term "metabolic syndrome" as used herein refers to a constellation of conditions that place people at high risk for coronary artery disease. These conditions include type 2 diabetes, obesity, high blood pressure, and a poor lipid profile with elevated LDL ("bad") cholesterol, low HDL ("good") cholesterol, and elevated triglycerides. All of these conditions are associated with high blood insulin levels. The fundamental defect in the metabolic syndrome is insulin resistance in both adipose tissue and muscle.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

The invention disclosed herein is further illustrated by the following non-limiting examples.

EXPERIMENTAL SECTION

General Methods

Analytical LC-MS data were obtained using one of the following methods.

Method A:

A PE Sciex API 150EX instrument equipped with atmospheric pressure photo ionisation and a Shimadzu LC-8A/SLC-10A LC system was used. Column: 4.6×30 mm Waters Symmetry C18 column with 3.5 µm particle size; Column temperature: 60° C.; Solvent system: A=water/trifluoroacetic acid (100:0.05) and B=water/acetonitrile/trifluoroacetic acid (5:95:0.035); Method: Linear gradient elution with A:B=90:10 to 0:100 in 2.4 minutes and with a flow rate of 3.3 mL/min.

Method B:

A PE Sciex API 300 instrument equipped with atmospheric pressure photo ionisation and a Waters UPLC system was used. Column: Acquity UPLC BEH $C_{18}$ 1.7 µm, 2.1×50 mm (Waters); Column temperature: 60° C.; Solvent system: A=water/trifluoroacetic acid (100:0.05) and B=water/acetonitrile/trifluoroacetic acid (5:95:0.035); Method: Linear gradient elution with A:B=90:10 to 0:100 in 1.0 minutes and with a flow rate of 1.2 mL/min.

Method C:

A PE Sciex API 150EX instrument equipped with atmospheric pressure photo ionisation and a Shimadzu LC-8A/SLC-10A LC system was used. Column: 4.6×30 mm Waters Symmetry C18 column with 3.5 µm particle size; Column temperature: 60° C.; Solvent system: A=water/trifluoroacetic acid (99.95:0.05) and B=methanol/trifluoroacetic acid (99.965:0.035); Method: Linear gradient elution with A:B=83:17 to 0:100 in 2.4 minutes and with a flow rate of 3.0 mL/min.

Preparative LC-MS-purification was performed on a PE Sciex API 150EX instrument with atmospheric pressure chemical ionization. Column: 50×20 mm YMC ODS-A with 5 µm particle size; Method: Linear gradient elution with A:B=80:20 to 0:100 in 7 minutes and with a flow rate of 22.7 mL/minute. Fraction collection was performed by split-flow MS detection.

$^1$H NMR spectra were recorded at 500.13 MHz on a Bruker Avance AV500 instrument or at 250.13 MHz on a Bruker Avance DPX250 instrument. TMS was used as internal reference standard. Chemical shift values are expressed in ppm. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet, br s=broad singlet and br=broad signal.

Abbreviations are in accordance with to the ACS Style Guide: "The ACS Styleguide—A manual for authors and editors" Janet S. Dodd, Ed. 1997, ISBN: 0841234620.

General:

p-Toluene-sulfonyl hydrazide (98%) was from Avocado. 2-Phenyl-1H-Imidazole-4-Carbaldehyde was from ASDI.

Preparation of the Compounds of the Invention

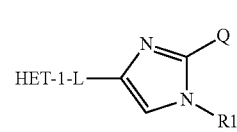

I

Compounds of the general formula I of the invention may be prepared as described in the following reaction schemes. Unless otherwise indicated, in the reaction schemes and discussion that follow, HET-1, $R_1$-$R_9$, -L-, Z and Y are as defined above.

Compounds of formula I, wherein -L- is —S—$CH_2$—, can be prepared by the coupling of a nucleophile of formula V or Va with an electrophile of formula VI, where X is a leaving group, e.g. Cl, Br, I, methanesulfonyl, 4-toluenesulfonyl, as shown in scheme 1. In the reaction between Va and VI, alkylation of the sulfur atom of Va with VI and ring closure to form the fused bicyclic triazole ring both take place under the same reaction conditions in a one-pot procedure.

Scheme 1

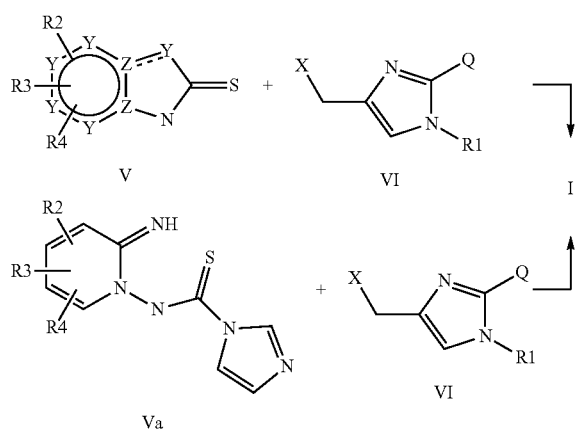

This reaction is typically carried out in a solvent such as 1-propanol, toluene, DMF, or acetonitrile, optionally in the presence of a carbonate base such as potassium carbonate or a tertiary amine base such as triethylamine or diisopropylethylamine (DIPEA), at a temperature ranging from about 0° C. to about 200° C., optionally under pressure in a closed vessel. Other suitable solvents include benzene, chloroform, dioxane, ethyl acetate, 2-propanol and xylene. Alternatively, solvent mixtures such as toluene/2-propanol can be used.

Compounds of formula V are either commercially available or can be prepared as described in the literature, see for example Brown et al. *Aust. J. Chem.* 1978, 31, 397-404; Yutilov et al. *Khim. Geter. Soedin.* 1988, 799-804; Wilde et al. *Bioorg. Med. Chem. Lett.* 1995, 5, 167-172; Kidwai et al. *J. Korean Chem. Soc.* 2005, 49, 288-291. Compounds of formula Va can be prepared as described in WO 96/01826 from the corresponding 1,2-diaminopyridines by reaction with thiocarbonyldiimidazole in a suitable solvent, such as chloroform, at a suitable temperature, such as room temperature or +40° C. The requisite 1,2-diaminopyridines are readily available from the corresponding commercially available 2-aminopyridines by reaction with a suitable N-amination reagent, such as O-(mesitylsulfonyl)hydroxylamine, in a suitable solvent, such as chloroform, at a suitable temperature, such as 0° C. or room temperature, see WO 96/01826.

2-Halomethyl-4-(aryl)-1H-triazoles of formula VI can be prepared by halogenation of the corresponding (2-Aryl-1H-imidazol-4-yl)-methanols or (2-heteroaryl-1H-imidazol-4-yl)-methanols using a suitable reagent, e.g. thionyl chloride, phosphorous trichloride, or phosphorous tribromide, optionally using a suitable solvent such as dichloromethane, using methods well known to chemists skilled in the art. The requisite (2-Aryl-1H-imidazol-4-yl)-methanols can be prepared by methods known in the art (see for example Journal of Medicinal Chemistry 1986, 29(2), 261-267; WO-2005014588A1). The requisite (2-Aryl-1H-imidazol-4-yl)-methanols or (2-heteroaryl-1H-imidazol-4-yl)-methanols are also readily available by reduction of the aldehydes XV (see scheme 4 below) by methods known to chemists skilled in the art, e.g. by reacting aldehydes of formula XV with a suitable reducing reagent, such as sodium borohydride, in a suitable solvent, such as THF or Methanol.

Compounds of formula I, wherein -L- is —CH$_2$—S—, can be prepared by the coupling of a nucleophile of formula XII with an electrophile of formula VIII as shown in scheme 2.

Scheme 2.

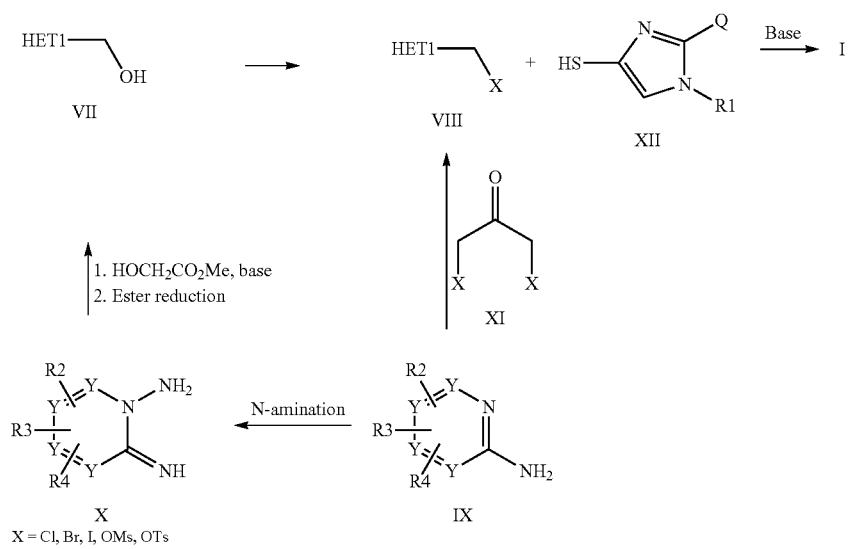

This reaction is typically carried out in a solvent such as 1-propanol, toluene, DMF, or acetonitrile, optionally in the presence of a carbonate base such as potassium carbonate or a tertiary amine base such as triethylamine or diisopropylethylamine (DIPEA), at a temperature ranging from about 0° C. to about 200° C., optionally under pressure in a closed vessel. Other suitable solvents include benzene, chloroform, dioxane, ethyl acetate, 2-propanol and xylene. Alternatively, solvent mixtures such as toluene/2-propanol can be used.

Some electrophiles of formula VIII are commercially available, and many others are known in the art, see for example JP 59176277. The electrophile VIII, where X is a leaving group, e.g. Cl, Br, I, methanesulfonyl, 4-toluenesulfonyl, can also be prepared by conversion of the primary alcohol of compounds of formula VII to said leaving group by methods known to chemists skilled in the art. Said methods can for example be selected from reacting compounds of formula VII with thionyl chloride, phosphorous trichloride, phosphorous tribromide, methanesulfonyl chloride, or 4-toluenesulfonyl chloride optionally in the presence of a suitable solvent, such as dichloromethane or 1,2-dichloroethane, and optionally in the presence of a base, such as triethylamine, diisopropylethylamine, or pyridine. Alternatively, electrophiles of formula VIII can be prepared by reacting commercially available aromatic amines of formula IX with 1,3-dihaloacetones of formula XI, e.g. 1,3-dichloroacetone, in a suitable solvent, such as 1,2-dimethoxyethane or ethanol, at a suitable temperature, such as room temperature or reflux. Some electrophiles of formula VII are commercially available, and many others are known in the art, see for example Tsuchiya, T.; Sashida, H. *J. Chem. Soc., Chem. Commun.* 1980, 1109-1110; Tsuchiya, T.; Sashida, H; Konoshita, A. *Chem. Pharm. Bull.* 1983, 31, 4568-4572. Alternatively, alcohols of formula VII can be prepared by reacting commercially available aromatic amines of formula IX with a suitable N-amination reagent, such as O-(mesitylsulfonyl)hydroxylamine, in a suitable solvent, such as chloroform, at a suitable temperature, such as 0° C. or room temperature, see WO 96/01826, to yield compounds of formula X. Said compounds of formula X can be converted into compounds of formula VII by reaction with methyl glycolate followed by reduction of the methyl ester to the requisite alcohol using a suitable reducing agent such as lithium aluminium hydride in a suitable solvent such as diethyl ether or tetrahydrofuran using methods known to chemists skilled in the art.

Compounds of formula XII can be prepared as described in the literature, see e.g. Zoete, Vincent et. al. *Journal of the Chemical Society, Perkin Transactions 1: Organic and Bio-Organic Chemistry* 1997, (20), 2983-2988.

Compounds of formula I, wherein R1 is not hydrogen, can be prepared by the alkylation of a compounds of formula I, wherein R1 is hydrogen, with an alkyl halide of formula XIII as shown in scheme 3.

Scheme 3.

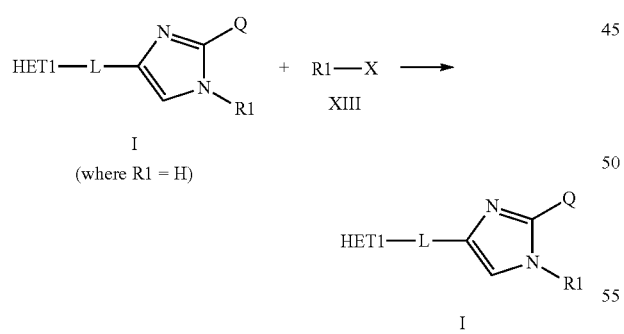

This reaction is typically carried out in a suitable solvent, such as dimethylformamide, dimethylacetamide, or acetonitrile, in the presence of a suitable base such as a carbonate base, e.g. potassium carbonate, or a tertiary amine base, e.g. triethylamine or diisopropylethylamine (DIPEA), at a temperature ranging from about 0° C. to about 100° C.

Compounds of formula I, wherein -L- is —CH=CH— or —CH$_2$—CH$_2$— can be prepared by the reaction sequence shown in scheme 4.

Scheme 4.

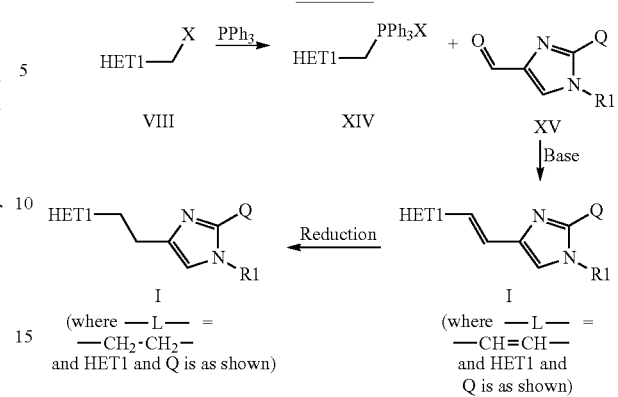

Specifically, compounds of formula I, wherein -L- is —CH$_2$—CH$_2$— can be prepared by reduction of an alkene of formula I, wherein -L- is —CH=CH—, by hydrogenation using a transition metal catalyst, such as palladium metal, together with a hydrogen source, such as hydrogen gas, ammonium hydrogen carbonate, or cyclohexadiene. Said alkenes of formula I, wherein -L- is —CH=CH— can be prepared by the Wittig reaction between a phosphonium salt of formula XIV and an aldehyde of formula XV in a suitable solvent, such as tetrahydrofuran, in the presence of a suitable base, such as 1,8-diazabicyclo[5.4.0]undec-7-ene. Phosphonium salt of formula XIV are readily available by reaction of compounds of formula VIII (see scheme 2 above) with triphenylphosphine by methods known to chemists skilled in the art.

Aldehydes of formula XV are readily available by oxidation of alcohols of formula VII (see scheme 2 above) by methods known to chemists skilled in the art, e.g. by reacting alcohols of formula VII with a suitable oxidizing agent, such as Dess-Martin periodinane, in a suitable solvent, such as dichloromethane or 1,2-dichlorethane. Or Aldehydes of formula XV are readily available by methods described in the literature see e.g. Dhainaut, A et. al. *Journal of Medicinal Chemistry*, 2000, 43, 2165-2175.

The invention disclosed herein is further illustrated by the following non-limiting examples.

Preparation of Intermediates

Example 1

2-Thiophen-2-yl-1H-imidazole-4-carbaldehyde

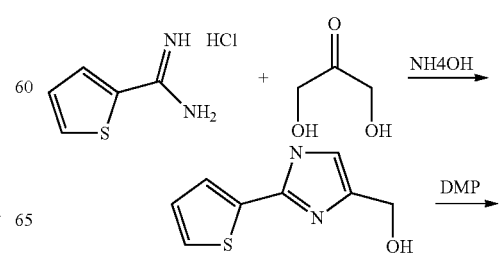

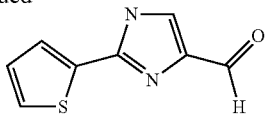

1,3-Dihydroxy-2-propanone (11.08 g, 123.0 mmol) was added to a stirred solution of 2-thiophenecarboxamidine hydrochloride in 12.4 M of Ammonia in water (200 mL) at rt. The solution was heated at reflux for 1 h. The solution was cooled to it and extracted with EtOAc (2×300 mL) and THF (300 ml). The combined organic phases were washed with brine (150 mL), dried (Na2SO4) and evaporated in vacuum to afford 6.4 g crude alcohol which was purified by silica gel chromatography (Eluent: 10% MeOH in EtOAc). Yield: 2.00 g of the alcohol (2-Thiophen-2-yl-1H-imidazol-4-yl)-methanol) (TLC: Rf aprox 0.1 in EtOAc).

Dess-Martin periodinane (4.71 g, 11.1 mmol) was added to a stirred suspension of (2-Thiophen-2-yl-1H-imidazol-4-yl)-methanol (2.00 g, 11.1 mmol) dissolved in Methylene chloride (111 mL) at it under Ar. The mixture turned dark and was stirred at rt ON. More DCM (100 ml) and sat NaHCO3 (100 mL) were added and the phases were separated after filtration to remove some solid. The organic layer was loaded onto silica gel and was purified by silica gel chromatography (Eluent: 0-100% EtOAc in n-heptane). Yield 0.57 g of the title compound as a red solid. LC-MS: m/z=178.6 (MH$^+$), $t_R$=0.31 min, method C.

Example 2

1-Methyl-2-thiazol-2-yl-1H-imidazole-4-carbaldehyde

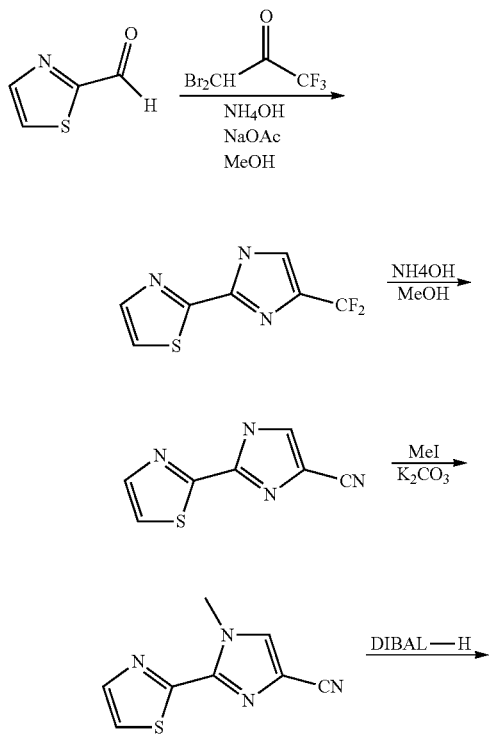

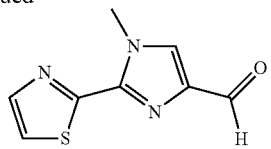

A modification (Alkylation step performed before DIBAL-H reduction) of the method of Baldwin et al. *J. Med. Chem.* 1975, 895 was used.

1,1-dibromotrifluoroacetone (26.24 g, 97.22 mmol) was added to a stirred solution of Sodium acetate (16.0 g, 194 mmol) in Water (90 mL) at rt. The solution was refluxed 30 min and then cooled to rt. The cooled solution was added to a stirred solution of 2-Formylthiazole (10.00 g, 88.39 mmol) in Methanol (400 mL) and 12.4 M of Ammonia in water (100 mL). The solution was stirred while kept at room temperature. The solution was rotovaped to 190 mL, and water (100 mL) was added. The solution was kept at 4 C for 30 min, and the resulting orange solid was filtered of. The orange solid was gently heated in water (approximately 100 ml). for 5 min (does not completely dissolve). The color changes to light brown. The solid was filtered of and dried in vacuum to afford 6.50 g of the intermediate 2-(4-Trifluoromethyl-1H-imidazol-2-yl)-thiazole. H-NMR (DMSO-d6) is similar to the published NMR (J. Med Chem (2000) 2165).

2-(4-Trifluoromethyl-1H-imidazol-2-yl)-thiazole (6.25 g, 28.5 mmol) was dissolved in methanol (300 mL) and 12.4 M of ammonia in water (40 mL) and Water (180 mL) was added. The solution was heated at 60 C ON. More 12 M NH3-water was added (40 ml) and the solution was heated at 70 C 5 h. The reaction was rotovaped to a smaller volume. A yellow solid precipitated out store at 4 C 2 h. A yellow powder was filtered off and dried in vac. Yield of 2-Thiazol-2-yl-1H-imidazole-4-carbonitrile: 5.54 g crude material.

Methyl iodide (4.06 g, 28.6 mmol) dissolved in DMF (8 ml) was added dropwise to a stirred solution of 2-Thiazol-2-yl-1H-imidazole-4-carbonitrile (5.31 g, 30.1 mmol) and Potassium carbonate (4.58 g, 33.1 mmol) dissolved in N,N-Dimethylformamide (50 mL). The mixture was stirred at 60° C. 1 h under Ar. Most of the DMF was removed in vacuum and the residue was partitioned between EtOAc (150 ml) and brine (50 mL). The organic phase was washed with more brine and dried (MgSO4). The solution was rotovaped and the crude product was purified by silica gel chromatography (Eluent: 20-50% EtOAc in n-heptane). Yield: 0.982 g yellow solid of 1-Methyl-2-thiazol-2-yl-1H-imidazole-4-carbonitrile. H-NMR: (DMSO-d6) δ 8.35 (s, 1H), 8.03 (d, 1H), 7.92 (d, 1H), 4.10 (s, 3H).

1.00 M of Diisobutylaluminum hydride in toluene (7.73 mL) was added to a stirred solution of 1-Methyl-2-thiazol-2-yl-1H-imidazole-4-carbonitrile (0.980 g, 5.15 mmol) dissolved in dry Tetrahydrofuran (10 mL) at −78° C. under Ar. The temp was slowly (approximately 1 hour) raised to −40 C. The cooling bath was removed and the mixture was quenched by adding MeOH (2.6 ml). The mixture was rotovaped and the crude product was chromatographed using Silica gel (Eluent: 0-30% MeOH in EtOAc) to afford 0.321 g impure material. This material was re-purified by silica gel chromatography (using EtOAc as eluent). Yield 140 mg of the title compound as a yellow solid. H-NMR (DMSO-d6): δ 9.76 (s, 1H), 8.28 (s, 1H) 8.04 (d, 1H), 7.90 (d, 1H), 4.12 (s, 3H). LC-MS: m/z=193.8 (MH$^+$), $t_R$=0.36 min, method C.

Example 3

2-Thiazol-5-yl-1H-Imidazole-4-carbaldehyde

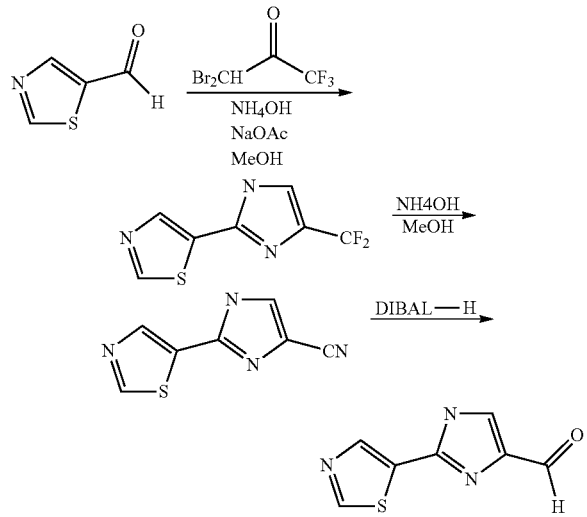

The method of Baldwin et al. *J. Med. Chem.* 1975, 895 was used.

The following intermediate are prepared analogously:

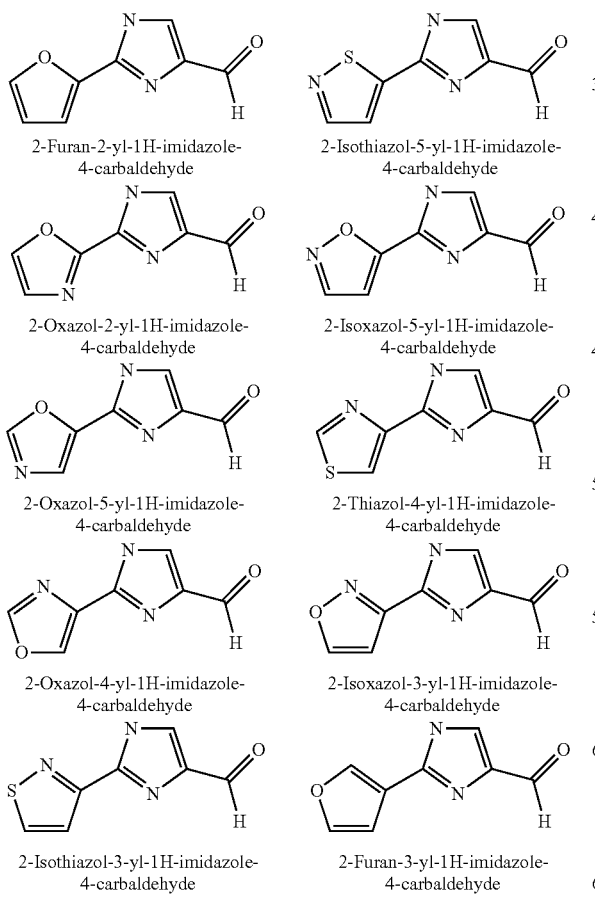

2-Furan-2-yl-1H-imidazole-4-carbaldehyde

2-Isothiazol-5-yl-1H-imidazole-4-carbaldehyde

2-Oxazol-2-yl-1H-imidazole-4-carbaldehyde

2-Isoxazol-5-yl-1H-imidazole-4-carbaldehyde

2-Oxazol-5-yl-1H-imidazole-4-carbaldehyde

2-Thiazol-4-yl-1H-imidazole-4-carbaldehyde

2-Oxazol-4-yl-1H-imidazole-4-carbaldehyde

2-Isoxazol-3-yl-1H-imidazole-4-carbaldehyde

2-Isothiazol-3-yl-1H-imidazole-4-carbaldehyde

2-Furan-3-yl-1H-imidazole-4-carbaldehyde

Example 4

1-Methyl-2-thiophen-2-yl-1H-Imidazole-4-carbaldehyde

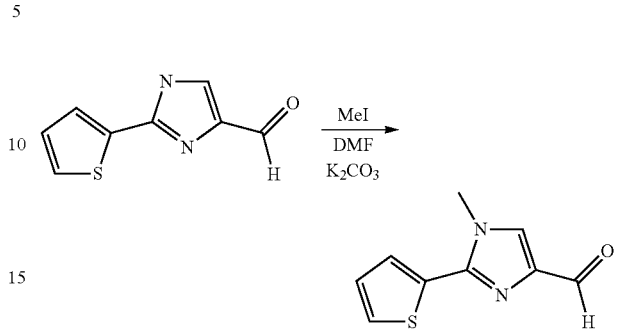

Methyl iodide (477 mg, 3.36 mmol) dissolved in DMF (0.5 ml) was added dropwise to a stirred solution of 2-Thiophen-2-yl-1H-imidazole-4-carbaldehyde (0.57 g, 3.2 mmol) and Potassium carbonate (0.486 g, 3.52 mmol) in dry N,N-Dimethylformamide (6 mL) at rt. The solution was stirred at 70° C. 3 h. Most of the DMF was evaporated off and the residue was partioned between EtOAc (50 ml) and brine (25 ml). The phases were separated and the organic phase was dried ($Na_2SO_4$) and the solvent was evaporated off. The crude product was purified by silica gel chromatography (Eluent: 50%-100% EtOAc in n-heptane). Yield: 211 mg of the title compound as an oil. H-NMR (DMSO-d6): δ 9.71 (s, 1H), 7.80 (s, 1H) 7.54 (m, 2H), 7.17 (m, 1H), 4.14 (s, 3H). LC-MS: m/z=192.9 ($MH^+$), $t_R$=0.34 min, method C. (211 mg of a fast eluting isomer (3-Methyl-2-thiophen-2-yl-3H-imidazole-4-carbaldehyde) was also isolated and discarded).

Example 5

2-Chloromethyl-5,7-dimethyl-[1,2,4]triazolo[1,5-a]pyrimidine

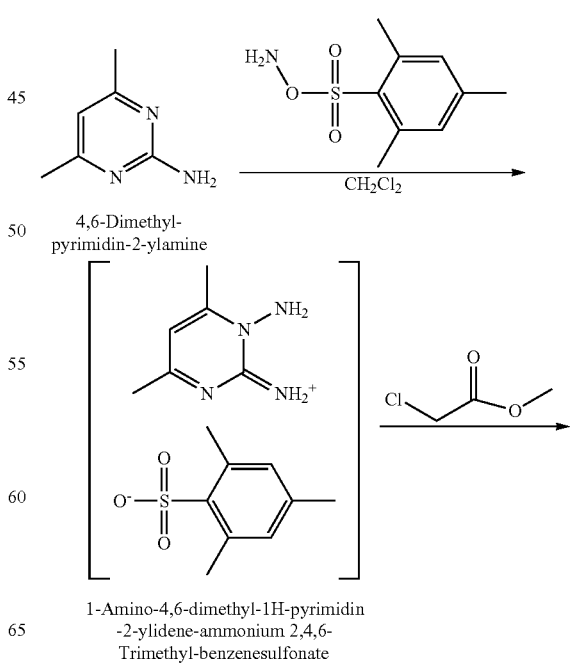

4,6-Dimethyl-pyrimidin-2-ylamine

1-Amino-4,6-dimethyl-1H-pyrimidin-2-ylidene-ammonium 2,4,6-Trimethyl-benzenesulfonate

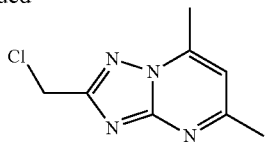

2-Chloromethyl-5,7-dimethyl-
[1,2,4]triazolo[1,5-a]pyrimidine

To a solution of 4,6-Dimethyl-pyrimidin-2-ylamine (25 g, 200 mmol) in 400 mL of $CH_2Cl_2$ was added dropwise a solution of hydroxylamine-2,4,6-Trimethyl-benzenesulfonate (105 g, 488 mmol) in 300 mL of $CH_2Cl_2$ at 0° C., and the mixture was stirred at 0° C. for 1 hour and filtered. The solid collected was washed with $CH_2Cl_2$ (100 mL) to give 1-Amino-4,6-dimethyl-1H-pyrimidin-2-ylidene-ammonium 2,4,6-trimethyl-benzenesulfonate (40 g, yield: 62%).

A mixture of 1-Amino-4,6-dimethyl-1H-pyrimidin-2-ylidene-ammonium 2,4,6-Trimethyl-benzenesulfonate (40 g, 0.1 mol) and NaOH (10 g, 0.2 mol) in 500 mL of EtOH was stirred at 50-60° C. for 1 hour. After chloroacetic acid methyl ester (16.6 g, 0.15 mol) was added, the resultant mixture was stirred at reflux for 4 hours. After being concentrated under reduce pressure, the residue was diluted with water (1000 mL) and extracted with $CH_2Cl_2$ (300 mL×3). The combined organic layers were washed with brine (200 mL), dried over $Na_2SO_4$, filtered, and concentrated under vacuum. The residue was purified by column chromatography on silica gel (petroleum ether/EtOAc=2/1) to give 2 g of 2-Chloromethyl-5,7-dimethyl-[1,2,4]triazolo[1,5-a]pyrimidine in 9% yield. $^1$H NMR (300 MHz, DMSO-d6): δ 8.55 (s, 1H), 6.25 (s, 2H), 4.05 (s, 3H), 3.95 (s, 3H): LC-MS (MH$^+$): m/z=196.9, $t_R$ (min, method A)=0.52

The following intermediates were prepared analogously:

7-Chloro-2-chloromethyl-5,8-dimethyl-[1,2,4]triazolo[1,5-c]pyrimidine from 6-Chloro-2,5-dimethyl-pyrimidine-4-ylamine prepared as described by Henze et al. J. Org. Chem 1952, 17, 1320-1327. 3.2% yield, LC-MS: m/z=231.5 (MH$^+$), $t_R$=1.13 min, method C 2-Chloromethyl-5,8-dimethyl-[1,2,4]triazolo[1,5-a]pyrazine from 2-amino-3,6-dimethylpyrazine. 60% yield, $^1$H NMR (500 MHz, CDCl$_3$): δ7.91 (s, 1H), 4.87 (s, 2H), 2.91 (s, 3H), 2.74 (s, 3H), LC-MS: m/z=196.9 (MH$^+$), $t_R$=0.64 min, method A 2-Chloromethyl-5,8-dimethyl-[1,2,4]triazolo[1,5-a]pyridine from 6-Chloro-5-ethyl-2-methyl-pyrimidin-4-ylamine. 21% yield, LC-MS: m/z=245.0 (MH$^+$), $t_R$=0.72 min, method A 2-Chloromethyl-8-methoxy-5-methyl-[1,2,4]triazolo[1,5-a]pyridine from 3-Methoxy-6-methyl-pyridin-2-ylamine. 64%, $^1$H NMR (500 MHz, DMSO-d$_6$): δ 7.11-7.08 (d, 1H), 7.01-6.98 (d, 1H), 4.93 (s, 2H), 3.98 (s, 3H), 2.61 (s, 3H)

2-Chloromethyl-8-methoxy-5-methyl-[1,2,4]triazolo[1,5-a]pyridine from 2-amino-6-methylpyridine, LC-MS: m/z=181.8 (MH+), $t_R$=0.64 min, method A.

2-Chloromethyl-8-methyl-[1,2,4]triazolo[1,5-a]pyridine from 2-amino-3-methylpyridine.

2-Chloromethyl-8-methoxy-[1,2,4]triazolo[1,5-a]pyridine from 2-amino-3-methoxypyridine, LC-MS: m/z=197.8 (MH+), $t_R$=0.40 min, method B.

2-Chloromethyl-8-ethyl-5-methyl-[1,2,4]triazolo[1,5-a]pyridine from 2-AMINO-3-ETHYL-6-METHYLPYRIDINE, LC-MS: m/z=209.8 (MH$^+$), $t_R$=0.60 min, method B.

The following compounds are known in the art:

2-Chloromethyl-1-phenyl-1H-benzoimidazole (JP 59176277).

1-Methyl-1,3-dihydro-benzoimidazole-2-thione (Wilde et al. Bioorg. Med. Chem. Lett. 1995, 5, 167-172).

1-Phenyl-1,3-dihydro-benzoimidazole-2-thione (Kidwai et al. J. Korean Chem. Soc. 2005, 49, 288-291).

[1,2,4]Triazolo[1,5-a]pyrimidine-2-thione (Brown et al. Aust. J. Chem. 1978, 31, 397-404).

1,3-Dihydro-imidazo[4,5-b]pyridine-2-thione (Yutilov et al. Khim. Geter. Soedin. 1988, 799-804).

Pyrazolo[1,5-a]pyridin-2-yl-methanol (Tsuchiya, T.; Sashida, H. J. Chem. Soc., Chem. Commun. 1980, 1109-1110; Tsuchiya, T.; Sashida, H;

Konoshita, A. Chem. Pharm. Bull. 1983, 31, 4568-4572).

Example 6

(5,8-Dimethyl-[1,2,4]triazolo[1,5-a]pyrazin-2-ylmethyl)-triphenyl-phosphonium; chloride

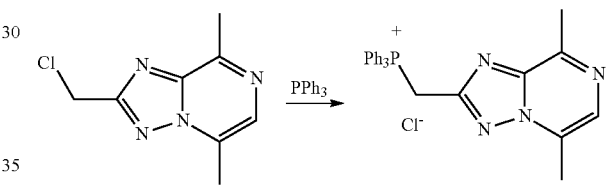

A solution of 2-chloromethyl-5,8-dimethyl-[1,2,4]triazolo[1,5-a]pyrazine (1.351 g, 6.87 mmol) and triphenylphosphine (1.80 g, 6.87 mmol) in acetonitrile 150 mL was heated at reflux for 12 h. The solvents were removed in vacuo and the residue slurried in ether, filtered and dried to yield (5,8-Dimethyl-[1,2,4]triazolo[1,5-a]pyrazin-2-ylmethyl)-triphenyl-phosphonium; chloride as an off white solid (2.412 g, 74.9%). LC-MS: m/z=423.2 ([M-Cl]$^+$), $t_R$=0.86 min, method A.

The following intermediates were prepared analogously:

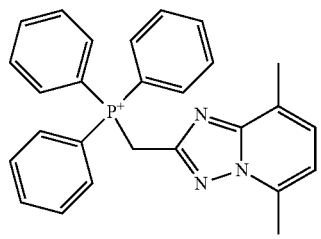

(5,8-Dimethyl-[1,2,4]triazolo[1,5-a]pyridin-2-ylmethyl)-triphenyl-phosphonium chloride from 2-Chloromethyl-5,8-dimethyl-[1,2,4]triazolo[1,5-a]pyridine, LC-MS: m/z=422.2 (MH$^+$), $t_R$=1.02 min, method A

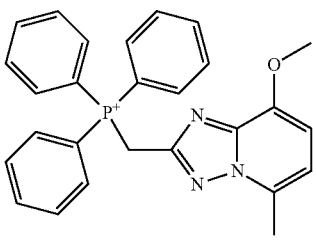 [SMILES: COc1ccc(C)n2nc(C[P+](c3ccccc3)(c3ccccc3)c3ccccc3)nc12]

(8-Methoxy-5-methyl-[1,2,4]triazolo[1,5-a]pyridin-2-yl-methyl)-triphenyl-phosphonium chloride from 2-Chloromethyl-8-methoxy-5-methyl-[1,2,4]triazolo[1,5-a]pyridine, LC-MS: m/z=438.4 (MH$^+$), $t_R$=0.96 min, method A

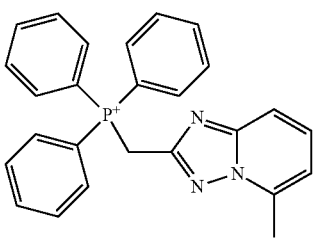 [SMILES: Cc1cccc2nc(C[P+](c3ccccc3)(c3ccccc3)c3ccccc3)nn12]

(5-Methyl-[1,2,4]triazolo[1,5-a]pyridin-2-ylmethyl)-triphenyl-phosphonium chloride from 2-Chloromethyl-5-methyl-[1,2,4]triazolo[1,5-a]pyridine, LC-MS: m/z=408.4 (MH$^+$), $t_R$=0.88 min, method A

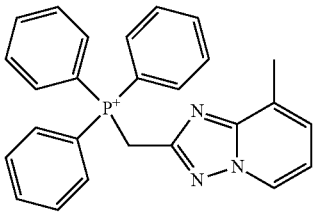 [SMILES: Cc1cccn2nc(C[P+](c3ccccc3)(c3ccccc3)c3ccccc3)nc12]

(8-Methyl-[1,2,4]triazolo[1,5-a]pyridin-2-ylmethyl)-triphenyl-phosphonium chloride from 2-Chloromethyl-8-methyl-[1,2,4]triazolo[1,5-a]pyridine, LC-MS: m/z=408.2 (MH$^+$), $t_R$=0.59 min, method B.

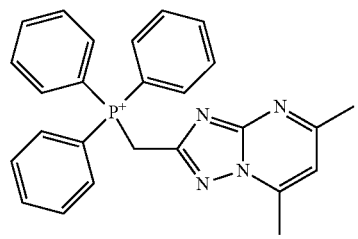 [SMILES: Cc1cc(C)n2nc(C[P+](c3ccccc3)(c3ccccc3)c3ccccc3)nc2n1]

(5,7-Dimethyl-[1,2,4]triazolo[1,5-a]pyrimidin-2-ylmethyl)-triphenyl-phosphonium chloride from 2-Chloromethyl-5,7-dimethyl-[1,2,4]triazolo[1,5-a]pyrimidine, LC-MS: m/z=423.3 (MH$^+$), $t_R$=0.85 min, method A

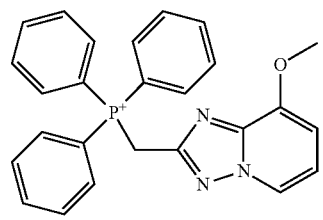 [SMILES: COc1cccn2nc(C[P+](c3ccccc3)(c3ccccc3)c3ccccc3)nc12]

(8-Methoxy-[1,2,4]triazolo[1,5-a]pyridin-2-ylmethyl)-triphenyl-phosphonium chloride from 2-Chloromethyl-8-methoxy-[1,2,4]triazolo[1,5-a]pyridine, LC-MS: m/z=423.9 (MH$^+$), $t_R$=0.55 min, method B

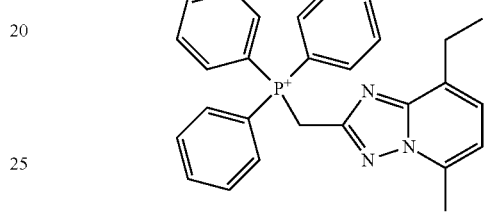

(8-Ethyl-5-methyl-[1,2,4]triazolo[1,5-a]pyridin-2-ylmethyl)-triphenyl-phosphonium chloride from 2-Chloromethyl-8-ethyl-5-methyl-[1,2,4]triazolo[1,5-a]pyridine, LC-MS: m/z=423.9 (MH$^+$), $t_R$=0.55 min, method B Preparation of the Compounds of the Invention Example 7

5,8-Dimethyl-2-[2-(2-phenyl-1H-imidazol-4-yl)-ethyl]-[1,2,4]triazolo[1,5-a]pyrazine

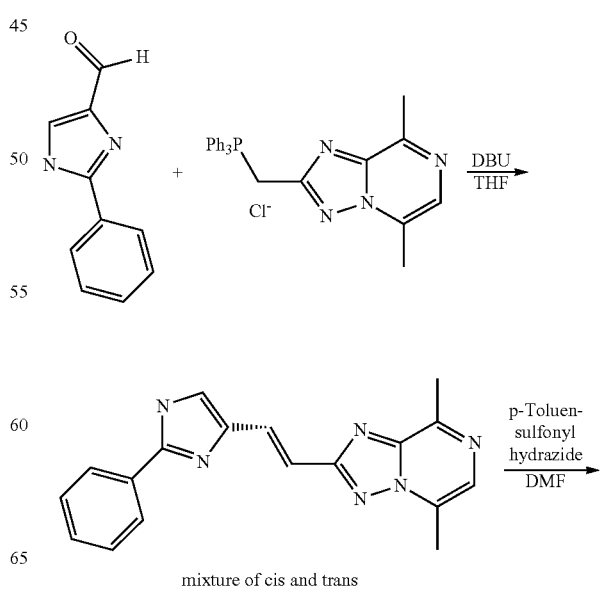

mixture of cis and trans

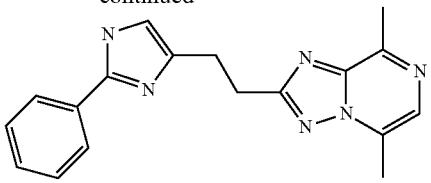

1,8-Diazabicyclo[5.4.0]undec-7-ene (0.087 mL, 0.58 mmol) was added to a stirred suspension of (5,8-Dimethyl-[1,2,4]triazolo[1,5-a]pyrazin-2-ylmethyl)-triphenyl-phosphonium; chloride (0.27 g, 0.58 mmol) and 2-Phenyl-1H-imidazole-4-carbaldehyde (0.100 g, 0.581 mmol) in dry THF (8 mL) and the mixture was stirred at room temperature under an atmosphere of Argon overnight. Some solid was filtered off and the solvent was removed in vac. The remanens was dissolved in DCM, and purified by silica gel chromatography (Eluent: 0-100% EtOAc in n-heptane). Yield: 97 mg of the intermediate as a cis/trans mixture as an oil (53%).

This material (0.090 g, 0.28 mmol) was dissolved in DMF (8 mL) and p-Toluenesulfonylhydrazide (0.16 g, 0.85 mmol) was added and the reaction was stirred at 120° C. 8 h under Ar. The solution was allowed to reach room temperature and stirred overnight. More p-Toluenesulfonyl hydrazide (0.08 g) was added, and the reaction mixture was at 120° C. 6 h under Ar. DMF was evaporated and the residue was dissolved in EtOAc (20 ml) and extracted with sat NaHCO3 (2×20 ml). The organic phase was washed with brine, dried (MgSO4) and was rotovaped. The crude product was purified by silica gel chromatography (Eluent: 0-100% EtOAc in n-heptane). Yield: 40 mg (40%) as an off white solid. LC-MS: m/z=319.2 (MH$^+$), $t_R$=0.63 min, method E. $^1$H NMR (600 MHz, CDCl$_3$): δ 7.90 (m, 3H), 7.43 (m, 2H), 7.35 (m, 1H), 6.96 (s, 1H), 3.40 (m, 2H), 3.22 (m, 2H) 2.98 (s, 3H), 2.75 (s, 3H).

The Following compounds were prepared analogously:
5,8-Dimethyl-2-[2-(1-methyl-2-phenyl-1H-imidazol-4-yl)-ethyl]-[1,2,4]triazolo[1,5-a]pyrazine (2), LC-MS: m/z=333.3 (MH$^+$), $f_R$=0.56 min, method E.
8-Ethyl-5-methyl-2-[2-(1-methyl-2-phenyl-1H-imidazol-4-yl)-ethyl]-[1,2,4]triazolo[1,5-a]pyridine (3), LC-MS: m/z=345.9 (MH$^+$), $t_R$=0.49 min, method C.
5,8-Dimethyl-2-[2-(1-methyl-2-thiophen-2-yl-1H-imidazol-4-yl)-ethyl]-[1,2,4]triazolo[1,5-a]pyrazine (4), LC-MS: m/z=338.8 (MH$^+$), $t_R$=0.35 min, method C.

Example 8

5,8-Dimethyl-2-[2-(1-methyl-2-thiazol-2-yl-1H-imidazol-4-yl)-ethyl]-[1,2,4]triazolo[1,5-a]pyrazine

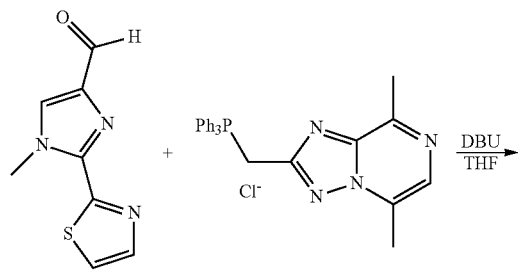

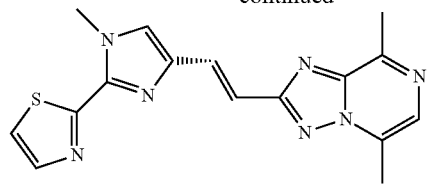

mixture of cis and trans

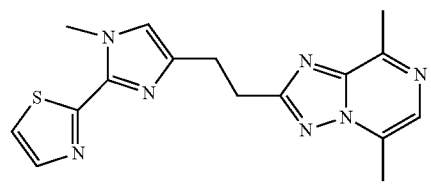

1,8-Diazabicyclo[5.4.0]undec-7-ene (0.109 mL, 0.72 mmol) was added to a stirred suspension of (5,8-Dimethyl-[1,2,4]triazolo[1,5-a]pyrazin-2-ylmethyl)-triphenyl-phosphonium; chloride (332 mg, 0.72 mmol) and 1-Methyl-2-thiazol-2-yl-1H-imidazole-4-carbaldehyde (140 mg, 0.72 mmol) in dry THF (18 mL) and the mixture was stirred at room temperature under an atmosphere of Argon 2 h. The solvent was removed in vac. The remanens was dissolved in DCM, and purified by silica gel chromatography (Eluent: 0-10% MeOH in EtOAc). Yield: 102 mg of the intermediate cis/trans mixture as a white solid (42%).

This material (102 mg, 0.30 mmol) was dissolved in DCM (5 mL) and MeOH (5 ml) and 10% Pd/C (35 mg) was added and the reaction was hydrogenated at 1.8 bar on a parr shaker ON. The catalyst was filtered off and the solvent was removed in vac. The crude product was purified by silica gel chromatography (Eluent: 0-10% MeOH in EtOAc). Yield: 80 mg (78%) of the title product as an off white solid. LC-MS: m/z=339.9 (MH$^+$), $t_R$=0.35 min, method C. $^1$H NMR (600 MHz, DMSO-d$_6$): δ 7.95 (s, 1H), 7.91 (d, 1H), 7.73 (d, 1H), 7.15 (s, 1H), 3.97 (s, 3H), 3.21 (m, 2H), 3.04 (m, 2H), 2.75 (s, 3H), 2.65 (s, 3H).

The Following compounds were prepared analogously:
8-Methoxy-5-methyl-2-[2-(2-phenyl-1H-imidazol-4-yl)-ethyl]-[1,2,4]triazolo[1,5-a]pyridine, LC-MS: m/z=334.5 (MH$^+$), $t_R$=0.78 min, method E.
8-Methoxy-5-methyl-2-[2-(1-methyl-2-thiophen-2-yl-1H-imidazol-4-yl)-ethyl]-[1,2,4]triazolo[1,5-a]pyridine (7), LC-MS: m/z=354.4 (MH$^+$), $t_R$=0.41 min, method C.
8-Methoxy-5-methyl-2-[2-(2-phenyl-1H-imidazol-4-yl)-ethyl]-[1,2,4]triazolo[1,5-a]pyridine LC-MS: m/z (MH+)=334.159, tR (min)=0.78, method C.
8-Methoxy-5-methyl-2-[2-(1-methyl-2-phenyl-1H-imidazol-4-yl)-ethyl]-[1,2,4]triazolo[1,5-a]pyridine LC-MS: m/z (MH+)=348.1746, tR (min)=0.7, method C.
8-Ethyl-5-methyl-2-[2-(1-methyl-2-phenyl-1H-imidazol-4-yl)-ethyl]-[1,2,4]triazolo[1,5-a]pyridine LC-MS: m/z (MH+)=346.1953, tR (min)=0.49, method C.
5,8-Dimethyl-2-[2-(2-phenyl-1H-imidazol-4-yl)-ethyl]-[1,2,4]triazolo[1,5-a]pyrazine LC-MS: m/z (MH+)=319.1593, tR (min)=0.63, method C.
5,8-Dimethyl-2-[(2-(1-methyl-2-phenyl-1H-imidazol-4-yl)-ethyl]-[1,2,4]triazolo[1,5-a]pyrazine LC-MS: m/z (MH+)=333.1749, tR (min)=0.56, method C.
8-Methoxy-5-methyl-2-[2-(1-methyl-2-thiophen-2-yl-1H-imidazol-4-yl)-ethyl]-[1,2,4]triazolo[1,5-a]pyridine LC-MS: m/z (MH+)=354.131, tR (min)=0.41, method C.

8-Methoxy-5-methyl-2-[2-(3-methyl-2-thiophen-2-yl-3H-imidazol-4-yl)-ethyl]-[1,2,4]triazolo[1,5-a]pyridine LC-MS: m/z (MH+)=354.2, tR (min)=0.4, method C.

5,8-Dimethyl-2-[2-(1-methyl-2-thiophen-2-yl-1H-imidazol-4-yl)-ethyl]-[1,2,4]triazolo[1,5-a]pyrazine LC-MS: m/z (MH+)=338.8, tR (min)=0.35, method C.

5,8-Dimethyl-2-[2-(1-methyl-2-thiazol-2-yl-1H-imidazol-4-yl)-ethyl]-[1,2,4]triazolo[1,5-a]pyrazine LC-MS: m/z (MH+)=339.9, tR (min)=0.35, method C.

5,8-Dimethyl-2-[2-(2-thiazol-5-yl-1H-imidazol-4-yl-ethyl]-[1,2,4]triazolo[1,5-a]pyrazine LC-MS: m/z (MH+)=326.111, tR (min)=0.43, method C.

5,8-Dimethyl-2-[2-(2-thiazol-5-yl-1H-imidazol-4-yl)-ethyl]-[1,2,4]triazolo[1,5-a]pyridine LC-MS: m/z (MH+)=325.1157, tR (min)=0.76, method C.

5,8-Dimethyl-2-[2-(1-methyl-2-thiazol-5-yl-1H-imidazol-4-yl)-ethyl]-[1,2,4]triazolo[1,5-a]pyrazine LC-MS: m/z (MH+)=340.1266, tR (min)=0.45, method C.

2-[2-(2-Furan-2-yl-1-methyl-1H-imidazol-4-yl)-ethyl]-5,8-dimethyl-[1,2,4]triazolo[1,5-a]pyrazine LC-MS: m/z (MH+)=323.1542, tR (min)=0.36, method C.

5,8-Dimethyl-2-[2-(2-thiazol-4-yl-1H-imidazol-4-yl)-ethyl]-[1,2,4]triazolo[1,5-a]pyrazine LC-MS: m/z (MH+)=326.111, tR (min)=0.33, method C.

5,8-Dimethyl-2-[2-(2-thiazol-4-yl-1H-imidazol-4-yl)-ethyl]-[1,2,4]triazolo[1,5-a]pyridine LC-MS: m/z (MH+)=325.1157, tR (min)=0.39, method C.

2-[2-(2-Furan-2-yl-1-methyl-1H-imidazol-4-yl)-ethyl]-5,8-dimethyl-[1,2,4]triazolo[1,5-a]pyridine LC-MS: m/z (MH+)=322, tR (min)=0.43, method C.

5,8-Dimethyl-2-[2-(2-thiophen-2-yl-1H-imidazol-4-yl)-ethyl]-[1,2,4]triazolo[1,5-a]pyridine LC-MS: m/z (MH+)=323.9, tR (min)=0.43, method C.

5,8-Dimethyl-2-[2-(2-thiazol-2-yl-1H-imidazol-4-yl)-ethyl]-[1,2,4]triazolo[1,5-a]pyridine LC-MS: m/z (MH+)=324.8, tR (min)=0.4, method C.

2-[2-(2-Furan-2-yl-1H-imidazol-4-yl)-ethyl]-5,8-dimethyl-[1,2,4]triazolo[1,5-a]pyridine LC-MS: m/z (MH+)=308.2, tR (min)=0.41, method C.

2-[2-(2-Furan-3-yl-1H-imidazol-4-yl)-ethyl]-5,8-dimethyl-[1,2,4]triazolo[1,5-a]pyridine LC-MS: m/z (MH+)=308.2, tR (min)=0.41, method C.

5,8-Dimethyl-2-[2-(2-thiophen-2-yl-1H-imidazol-4-yl)-ethyl]-[1,2,4]triazolo[1,5-a]pyrazine LC-MS: m/z (MH+)=325.1157, tR (min)=0.4, method C.

5,8-Dimethyl-2-[2-(2-thiazol-2-yl-1H-imidazol-4-yl)-ethyl]-[1,2,4]triazolo[1,5-a]pyrazine LC-MS: m/z (MH+)=326.111, tR (min)=0.37, method C.

2-[2-(2-Furan-3-yl-1H-imidazol-4-yl)-ethyl]-5,8-dimethyl-[1,2,4]triazolo[1,5-a]pyrazine LC-MS: m/z (MH+)=309.1386, tR (min)=0.38, method C.

2-[2-(2-Furan-2-yl-1H-imidazol-4-yl)-ethyl]-5,8-dimethyl-[1,2,4]triazolo[1,5-a]pyrazine LC-MS: m/z (MH+)=309.1386, tR (min)=0.32, method C.

2-[2-(1H-Imidazol-4-yl)-ethyl]-5,8-dimethyl-[1,2,4]triazolo[1,5-a]pyrazine LC-MS: m/z (MH+)=243.3, tR (min)=0.24, method C.

5,8-Dimethyl-2-{2-[1-methyl-2-(5-methyl-furan-2-yl)-1H-imidazol-4-yl]-ethyl}-[1,2,4]triazolo[1,5-a]pyrazine LC-MS: m/z (MH+)=337.1, tR (min)=0.37, method C.

5,8-Dimethyl-2-[2-(1-methyl-2-thiazol-4-yl-1H-imidazol-4-yl)-ethyl]-[1,2,4]triazolo[1,5-a]pyrazine LC-MS: m/z (MH+)=340.1266, tR (min)=0.61, method C.

2-{2-[2-(4-Fluoro-phenyl)-1H-imidazol-4-yl]-ethyl}-5,8-dimethyl-[1,2,4]triazolo[1,5-a]pyrazine LC-MS: m/z (MH+)=337.1, tR (min)=0.36, method C.

Example 9

8-Methoxy-5-methyl-2-[2-(1-methyl-2-phenyl-1H-Imidazol-4-yl)-ethyl]-[1,2,4]triazolo[1,5-a]pyridine

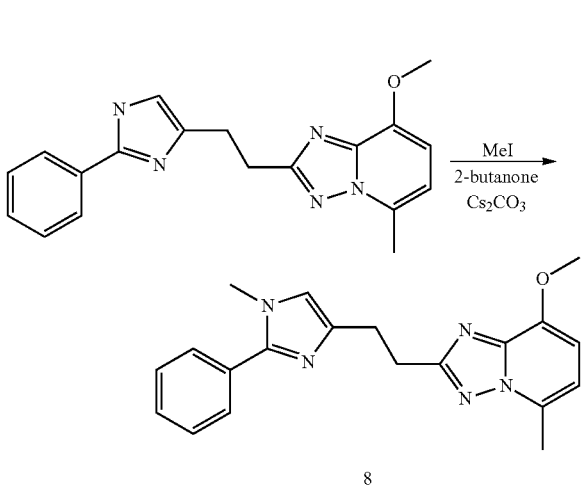

8

Methyl iodide (0.035 mL, 0.57 mmol) was added to a stirred suspension of 8-Methoxy-5-methyl-2-[2-(2-phenyl-1H-imidazol-4-yl)-ethyl]-[1,2,4]triazolo[1,5-a]pyridine (145 mg, 0.435 mmol) and Cs$_2$CO$_3$ (360 mg, 1.1 mmol) in 2-Butanone (10 mL). The mixture was heated at 50° C. for 7 hours under an atmosphere of Argon. The mixture was cooled to rt and the solvent was evaporated off. The crude product was dissolved in DCM and purified by silica gel chromatography (Eluent: 0-100% EtOAc in n-heptane, then changed to 0-5% MeOH in EtOAc). Yield: 31 mg (20%) of the title compound as an off white solid. LC-MS: m/z=348.2 (MH$^+$), t$_R$=0.70 min, method E.

Pharmacological Testing
PDE10A Enzyme

Active PDE10A enzyme is prepared in a number of ways for use in PDE assays (Loughney, K. et al. *Gene* 1999, 234, 109-117; Fujishige, K. et al. *Eur J Biochem.* 1999, 266, 1118-1127 and Soderling, S. et al. *Proc. Natl. Acad. Sci.* 1999, 96, 7071-7076). PDE10A can be expressed as full-length proteins or as truncated proteins, as long as they express the catalytic domain. PDE10A can be prepared in different cell types, for example insect cells or *E. coli*. An example of a method to obtain catalytically active PDE10A is as follows: The catalytic domain of human PDE10A (amino acids 440-779 from the sequence with accession number NP 006652) is amplified from total human brain total RNA by standard RT-PCR and is cloned into the BamH1 and Xho1 sites of the pET28a vector (Novagen). Expression in coli is performed according to standard protocols. Briefly, the expression plasmids are transformed into the BL21(DE3) *E. coli* strain, and 50 mL cultures inoculated with the cells allowed to grow to an OD600 of 0.4-0.6 before protein expression is induced with 0.5 mM IPTG. Following induction, the cells are incubated overnight at room temperature, after which the cells are collected by centrifugation. Cells expressing PDE10A are resuspended in 12 mL (50 mM TRIS-HCl-pH8.0, 1 mM MgCl$_2$ and protease inhibitors). The cells are lysed by sonication, and after all cells are lysed, TritonX100 is added according to Novagen protocols. PDE10A is partially purified on Q sepharose and the most active fractions were pooled.

PDE10A Inhibition Assay

A PDE10A assay may for example, be performed as follows: The assay is performed in 60 uL samples containing a fixed amount of the relevant PDE enzyme (sufficient to convert 20-25% of the cyclic nucleotide substrate), a buffer (50 mM HEPES7.6; 10 mM MgCl$_2$; 0.02% Tween20), 0.1 mg/ml BSA, 225 pCi of $^3$H-labelled cyclic nucleotide substrate, tritium labeled cAMP to a final concentration of 5 nM and varying amounts of inhibitors. Reactions are initiated by addition of the cyclic nucleotide substrate, and reactions are allowed to proceed for one hr at room temperature before being terminated through mixing with 15 uL 8 mg/mL yttrium silicate SPA beads (Amersham). The beads are allowed to settle for one hr in the dark before the plates are counted in a Wallac 1450 Microbeta counter. The measured signal can be converted to activity relative to an uninhibited control (100%) and IC$_{50}$ values can be calculated using the Xlfit extension to EXCEL.

Phencyclidine (PCP) Induced Hyperactivity

Male mice (NMRI, Charles River) weighing 20-25 g are used. Eight mice are used in each group receiving the test compound (5 mg/kg) plus PCP (2.3 mg/kg) including the parallel control groups receiving the vehicle of the test compound plus PCP or vehicle injections only. The injection volume is 10 ml/kg. The experiment is made in normal light conditions in an undisturbed room. The test substance is injected per oss 60 min before injection of PCP, which is administered subcutaneous.

Immediately after injection of PCP the mice are placed individually in special designed test cage (20 cm×32 cm). The activity is measured by 5×8 infrared light sources and photocells spaced by 4 cm. The light beams cross the cage 1.8 cm above the bottom of the cage. Recording of a motility count requires interruption of adjacent light beams, thus avoiding counts induced by stationary movements of the mice.

Motility is recorded in 5 min intervals for a period of 1 hour. The drug effect is calculated on the total counts during the 1 hour behavioral test period in the following manner:

The mean motility induced by vehicle treatment in the absence of PCP is used as baseline. The 100 percent effect of PCP is accordingly calculated to be total motility counts minus baseline. The response in groups receiving test compound is thus determined by the total motility counts minus baseline, expressed in percent of the similar result recorded in the parallel PCP control group. The percent responses are converted to percent inhibition.

What is claimed:

1. A method of treating a subject suffering from a psychiatric disorder, comprising administering to said subject a therapeutically effective amount of the compound of formula I

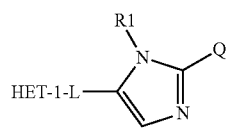

wherein HET-1 is a heteroaromatic group of formula II containing from 2 to 4 nitrogen atoms:

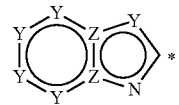

wherein Y is N or CH,
wherein Z is N or C,
and wherein HET-1 may optionally be substituted with up to three $R_7$, $R_8$ and $R_9$ substituents individually selected from hydrogen, $C_1$-$C_6$ alkyl; halogen; cyano, halo($C_1$-$C_6$)alkyl; aryl, alkoxy and $C_1$-$C_6$ hydroxyalkyl, and wherein * denotes the attachment point,
Q is phenyl, optionally substituted with one, two or three $R_2$, $R_3$, $R_4$, $R_5$ and $R_6$ substituents, wherein $R_2$, $R_3$, $R_4$, $R_5$ and $R_6$ are each selected independently from hydrogen, $C_1$-$C_6$ alkoxy and halogen; or a monocyclic 5-membered or 6-membered heteroaromatic group containing 1 or 2 heteroatoms,
-L- is a linker selected from —S—CH$_2$—, —CH$_2$—S—, —CH$_2$—CH$_2$—, —CH=CH—, and —C≡C—,
$R_1$ is selected from H, $C_1$-$C_6$ alkyl; $C_1$-$C_6$ alkyl($C_3$-$C_8$) cycloalkyl; $C_1$-$C_5$ hydroxyalkyl, CH$_2$CN, CH$_2$C(O)NH$_2$, $C_1$-$C_6$ arylalkyl, and $C_1$-$C_6$ alkyl-heterocycloalkyl,
wherein the psychiatric disorder is selected from the group consisting of schizophrenia; schizophreniform disorder; and schizoaffective disorder.

2. The method of claim 1 wherein the psychiatric disorder is schizophrenia.

3. The method of claim 2 wherein the schizophrenia is paranoid schizophrenia, disorganized schizophrenia, catatonic schizophrenia, undifferentiated schizophrenia, or residual type schizophrenia.

4. The method of claim 1 wherein the schizoaffective disorder is of the delusional type or the depressive type.

5. The method of claim 1 wherein the compound is selected from the group consisting of:
5,8-Dimethyl-2-[2-(2-phenyl-1H-imidazol-4-O-ethyl]-[1,2,4]triazolo[1,5-a]pyrazine;
5,8-Dimethyl-2-[2-(1-methyl-2-phenyl-1H-imidazol-4-yl)-ethyl]-[1,2,4]triazolo[1,5-a]pyrazine;
8-Ethyl-5-methyl-2-[2-(1-methyl-2-phenyl-1H-imidazol-4-yl)-ethyl]-[1,2,4]triazolo[1,5-a]pyridine;
5,8-Dimethyl-2-[2-(1-methyl-2-thiophen-2-yl-1H-imidazol-4-yl)-ethyl]-[1,2,4]triazolo[1,5-a]pyrazine;
5,8-Dimethyl-2-[2-(1-methyl-2-thiazol-2-yl-1H-imidazol-4-yl)-ethyl]-[1,2,4]triazolo[1,5-a]pyrazine;
8-Methoxy-5-methyl-2-[2-(2-phenyl-1H-imidazol-4-yl)-ethyl]-[1,2,4]triazolo[1,5-a]pyridine;
8-Methoxy-5-methyl-2-[2-(1-methyl-2-thiophen-2-yl-1H-imidazol-4-yl)-ethyl]-[1,2,4]triazolo[1,5-a]pyridine; and
8-Methoxy-5-methyl-2-[2-(1-methyl-2-phenyl-1H-imidazol-4-yl)-ethyl]-[1,2,4]triazolo[1,5-a]pyridine; and pharmaceutically acceptable salts thereof.

6. The method of claim 1, wherein the compound is administered in combination with one or more neuroleptic agents.

7. The method of claim 6 wherein the neuroleptic agent is selected from the group consisting of sertindole, olanzapine, risperidone, quetiapine, aripiprazole, haloperidol, clozapine, ziprasidone and osanetant.

* * * * *

UNITED STATES PATENT AND TRADEMARK OFFICE
CERTIFICATE OF CORRECTION

| | | |
|---|---|---|
| PATENT NO. | : 8,927,738 B2 | Page 1 of 1 |
| APPLICATION NO. | : 13/924712 | |
| DATED | : January 6, 2015 | |
| INVENTOR(S) | : Ask Puschl et al. | |

It is certified that error appears in the above-identified patent and that said Letters Patent is hereby corrected as shown below:

In the Claims

Amend Claim 1, column 34, line 24, to recite "$C_1$-$C_6$ hydroxyalkyl" in lieu of "$C_1$-$C_5$ hydroxyalkyl".
Amend Claim 5, column 34, line 40, to recite "5-8-Dimethyl-2-[2-(2-phenyl-1H-imidazol-4-yl)-ethyl]-[1,2,4]triazolo[1,5-a]pyrazine" in lieu of "5-8-Dimethyl-2-[2-(2-phenyl-1H-imidazol-4-O-ethyl]-[1,2,4]triazolo[1,5-a]pyrazine".

Signed and Sealed this
Fourteenth Day of April, 2015

Michelle K. Lee
*Director of the United States Patent and Trademark Office*